(12) United States Patent
Dewald et al.

(10) Patent No.: US 7,252,644 B2
(45) Date of Patent: Aug. 7, 2007

(54) SYSTEM AND METHODS TO OVERCOME GRAVITY-INDUCED DYSFUNCTION IN EXTREMITY PARESIS

(75) Inventors: Julius P. A. Dewald, Downers Grove, IL (US); Wilhelmus J. Lam, Orchard Park, NY (US)

(73) Assignees: Northwestern University, Evanston, IL (US); The Rehabilitation Institute, Chicago, IL (US); Lam Design Management LLC, Orchard Park, NY (US)

( * ) Notice: Subject to any disclaimer, the term of this patent is extended or adjusted under 35 U.S.C. 154(b) by 26 days.

(21) Appl. No.: 11/239,709

(22) Filed: Sep. 29, 2005

(65) Prior Publication Data

US 2006/0079817 A1    Apr. 13, 2006

Related U.S. Application Data

(60) Provisional application No. 60/614,928, filed on Sep. 29, 2004.

(51) Int. Cl.
*A61H 1/02*    (2006.01)
(52) U.S. Cl. ............................ 601/5; 601/23; 601/33
(58) Field of Classification Search ............ 601/5, 601/23, 27, 33, 34, 26; 602/5, 23, 26; 607/48–49; 482/8, 901–902, 9
See application file for complete search history.

(56) References Cited

U.S. PATENT DOCUMENTS

| | | | |
|---|---|---|---|
| 4,398,889 A | 8/1983 | Lam et al. | |
| 4,936,299 A | 6/1990 | Erlandson | |
| 5,201,772 A * | 4/1993 | Maxwell | 482/8 |
| 5,421,798 A | 6/1995 | Bond et al. | |
| 5,466,213 A | 11/1995 | Hogan et al. | |
| 5,476,441 A * | 12/1995 | Durfee et al. | 602/23 |
| 5,484,389 A * | 1/1996 | Stark et al. | 601/34 |
| 5,830,160 A | 11/1998 | Reinkensmeyer | |
| 6,413,190 B1 | 7/2002 | Wood et al. | |
| 6,613,000 B1 | 9/2003 | Reinkensmeyer et al. | |
| 6,636,161 B2 | 10/2003 | Rosenberg | |
| 6,697,043 B1 | 2/2004 | Shahoian | |

* cited by examiner

*Primary Examiner*—Quang D. Thanh
(74) *Attorney, Agent, or Firm*—Bell & Associates; Matthew Kaser

(57) ABSTRACT

The present invention relates to a system for use in rehabilitation and/or physical therapy for the treatment of injury or disease. The system can overcome gravity-induced dysfunction in extremity paresis following stroke or other neurological disorders.

19 Claims, 12 Drawing Sheets
(2 of 12 Drawing Sheet(s) Filed in Color)

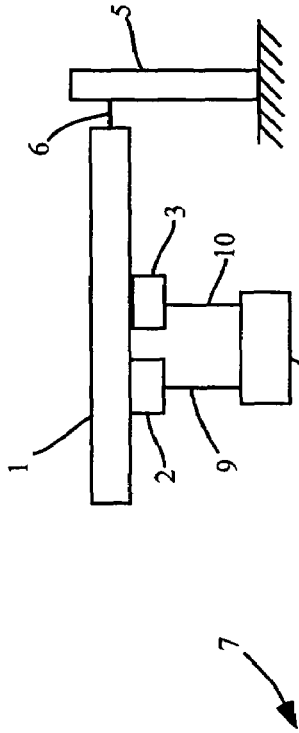
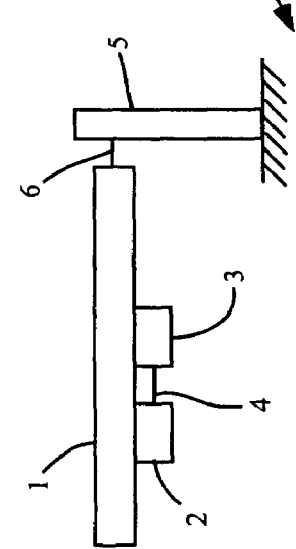
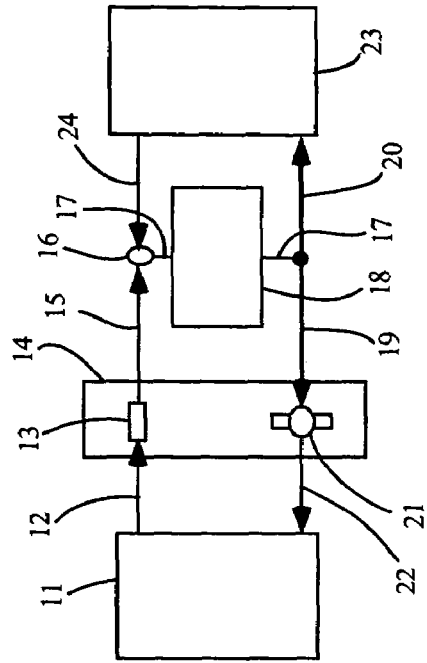
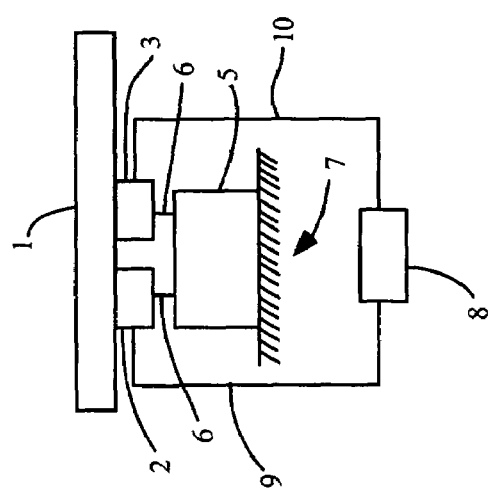

SYSTEM AND METHODS TO OVERCOME GRAVITY-INDUCED DYSFUNCTION IN EXTREMITY PARESIS

The present application claims priority to U.S. Provisional Patent Application Ser. No. 60/614,928 entitled "Devices and Methods to Overcome Gravity-Induced Dysfunction in Upper Extremity Paresis", filed Sep. 29, 2004, which is herein incorporated by reference in its entirety for all purposes.

The United States government has certain rights to this invention pursuant to Grant No. H133G030143 from the National Institutes of Disability and Rehabilitation Research to Northwestern University.

FIELD OF THE INVENTION

The invention relates to the field of rehabilitation and/or physical therapy for the treatment of injury and/or disease using a haptic system that is used to train and/or assist an individual having a neurological condition. In one aspect the invention provides an assistive robotic device in combination with a 3-dimensional virtual reality workspace. More specifically, the invention relates to a system and method to overcome gravity-induced dysfunction in upper extremity paresis.

BACKGROUND OF THE INVENTION

Disturbances in movement coordination are the least well understood but often the most debilitating with respect to functional recovery following brain injury. These deficits in coordination are expressed in the form of abnormal muscle synergies and result in limited and stereotypic movement patterns that are functionally disabling. The result of these constraints in muscle synergies is an abnormal coupling between shoulder abduction and elbow flexion in the arm, which significantly reduces a stroke survivor's reaching space when he/she lifts up the weight of the impaired arm against gravity. Current neurotherapeutic approaches to mitigate these abnormal synergies have produced, at best, limited functional recovery.

In the leg the expression of abnormal synergies results in coupling between hip/knee extension with hip adduction. The result of this is a reduced ability of activating hip abductor muscles in the impaired leg during stance.

Disturbances of Voluntary Movement in Hemiparetic Stroke

A detailed qualitative description of the abnormal movement patterns in the impaired limb, and the natural history of the evolution of the various components of these abnormal clinical signs was first provided by Twitchell in 1951, in which he delineated both the major features of the movement disturbance, and the time course of recovery from stroke (Twitchell (1951) Brain 74: 443–480). A prominent feature of the disturbed movement patterns was the emergence of "stereotypic" movements, in which there appeared to be a relatively tight coupling of motion at adjacent joints in the upper and lower limbs.

Brunnstrom subsequently classified these abnormal stereotypic movement patterns into so called "synergies" which were broadly of either flexor or extensor type (Brunnstrom (1970) In: "Movement therapy in hemiplegia: a neurophysiological approach" Harper & Row, Publishers Inc., Hagerstown Md.). This qualitative classification of abnormal synergies, summarized in Table 1, has received limited modification or study by other investigators.

TABLE 1

Upper Limb synergies in hemiparetic stroke after Brunnstrom (1970, supra)

| Extension synergy | Flexion synergy |
|---|---|
| Arm | Arm |
| Shoulder Girdle protraction adduction internal rotation Elbow extension pronation | Shoulder Girdle Retraction abduction to 90° external rotation Elbow Flexion Supination |
| Leg | Leg |
| Hip extension adduction internal rotation Knee extension | Hip extension adduction internal rotation Knee extension |

Recent treatment approaches for hemiparetic upper extremity such as "motor relearning program", electromyographic (EMG)-triggered/functional electrical stimulation, repeated mental practice, constraint-induced movement therapy, robot-aided sensory-motor training and bilateral arm training focus on task-specific repetition, increased intensity, and/or exercise in a real-world context. (See, for example, Langhammer and Stanghelle (2000) Clin. Rehabil. 14: 361–369; Cauraugh et al. (2000) Stroke 31: 1360–1364; Page et al. (2001) Phys. Ther. 81: 1455–1462; Miltner et al. (1999) Stroke 30: 586–592; van der Lee et al. (1999) Stroke 30: 2369–2375; Volpe et al. (2000) Neurology 54: 1938–1944; Volpe et al. (1999) Neurology 53: 1874–1876; Whitall et al. (2000) Stroke 31: 2390–2395; and Richards and Pohl (1999) Clin Geriatr Med 15: 819–832; Woldag and Hummelsheim (2002) J. Neurol. 249: 518–528) Despite favorable mounting evidence for the newer treatment models, none of the current neurorehabilitation techniques directly address the presence of abnormal synergistic patterns that constrain functional reaching (Dewald et al. (200 1) Topics in Stroke Rehabilitation 8: 1–11). Interventions that target abnormal synergistic movement patterns may ameliorate functional reaching and greatly benefit individuals with chronic stroke-induced movement discoordination.

In the lower limb recent findings from basic science provide preliminary evidence that functional locomotor recovery is possible after stroke or spinal cord injury when intense and accurate afferent input is provided in a task-specific and repetitive manner, Treadmill training is an example of a therapeutic modality that is derived from studies of adult cats with a low thoracic spinal transection who recovered the ability to step on a moving treadmill belt after they were trained on the treadmill and provided with truncal support, stimulation to recover extensor activity, and assistance in paw placement (Barbeau and Rossignol (1987) Brain Res. 412: 84–95; de Leon et al. (1998a) J. Neurophysiol. 80: 83–91; de Leon et al. (1998b) J. Neurophysiol. 79: 1329–1340; Lovely, et al., (1986) Exp. Neurol. 92: 421–435). Investigators have found that the spinal locomotor pools, which include a central pattern generator for automatic, alternating flexor and extensor leg muscle activity, are highly responsive to phasic segmental sensory inputs associated with walking and demonstrate evidence of learning during step training (Edgerton et al. (1997a) Adv Neurol.

72: 233–247; Edgerton et al. (1997b). Repetitive practice of the task was essential to the learning.

Barbeau and colleagues were the first investigators to translate this paradigm to human application for re-training walking after spinal cord injury and stroke (Barbeau et al., (1987) Brain Res. 437: 83–96; Finch et al. (1991) Phys. Ther. 71: 842–855; Visintin and Barbeau (1989) Can. J. Neurol. Sci. 16: 315–325; Visintin and Barbeau (1994) Paraplegia 32: 540–553). In their initial work, Barbeau et al. (Barbeau et al., (1987) supra) suspended the consumer over a treadmill using an overhead lift for body-weight support and clinician-provided assistance to the legs.

Task-specific training appears to be critical to the success of a locomotor training intervention post-stroke (Richards et al. (1993) Arch. Phys. Med. Rehabil. 74: 612–620). Treadmill training is a method of locomotor training that closely simulates the sensory elements specific to walking such as load on the lower extremities, upright trunk posture, proper lower limb kinematics, and normal walking speeds to generate effective lower limb stepping (Edgerton et al. (1997) supra; Behrman and Harkema (2000) Phys. Ther. 80: 688–700).

Within the past 10 years, there have been many studies that have specifically investigated the effects of treadmill training with or without body weight support (BWS) on post-stroke locomotor recovery. Treadmill training (with or without BWS) appears to be more effective than conventional therapy alone in locomotor recovery after stroke (Richards et al. (1993) supra; Hesse et al. (1995a) Stroke 26: 976–981; Hesse et al. (1995b); Laufer et al. (2001) J. Rehabil. Res. Dev. 38: 69–78; Pohl (2002) Stroke 33: 553–558; Sullivan et al. (2002) Arch. Phys. Med. Rehabil. 83: 683–691). While there is building evidence that this therapeutic modality may be beneficial in improving locomotor ability after stroke, there is little agreement or systematic study of the optimal training parameters to maximize functional outcomes (Tuszynski, Edgerton, and Dobkin (1999) J. Spinal Cord Med. 22: 143). None of the current studies have incorporated abnormal muscle coactivation patterns and associated joint toques in the lower extremity. We have quantitative evidence that abnormal coupling between hip and knee extension and hip adduction exists. Furthermore, we have preliminary data that this abnormal coupling reduces the ability to generate hip abduction while stading on the paretic leg. This results then in the inability to keep the pelvis horizontal and could result in the stroke subject falling towards the affected side. As in the case of the arm, interventions that target abnormal synergistic movement patterns may ameliorate balance and greatly benefit individuals with chronic stroke-induced movement discoordination.

Implementation of current treatment philosophies is more dependent on the therapist's background and training rather than clear clinical indications or objective and quantitative measures. Furthermore, there is no consensus in the literature to support one approach over the other or even a gold standard objective measure of their effectiveness in increasing functional recovery. Heinemann et al. reported on the relationship between functional status at discharge and intensities of therapies received during the patient's in-patient medical rehabilitation (Heinemann et al. (1995) Am. J. Phys. Med. Rehabil. 74: 315–326). The results for a group of 140 patients with traumatic brain injury (TBI) identified no significant correlation between functional outcome and the intensity of therapies. The apparent lack of benefit related to intensity of therapies may be due to such factors as spontaneous recovery, lack of adequate level of intensity based on the stroke patient's absolute tolerance, and most importantly, to inadequate measurement tools, which are subjective and non-quantitative, and do not possess the discrimination power required to detect meaningful functional change. Furthermore, most current approaches may not be effective in promoting the use of more functional elbow-shoulder torque combinations because of the implementation of limited, poorly controlled exercise sequences. None of the current neurorehabilitation techniques encourage movements outside abnormal synergic patterns in a rigorous and quantifiable way.

Evidence for Motor Learning and Strength Training Capabilities Following Stroke

We have evidence from previous work that, depending on the lesion location, hemiparetic stroke subjects are able to adapt to novel force perturbations applied to their impaired arms during reaching and retrieval movements (see Krebs et al. (1996) 18th Annual Conference of IEEE-EMBS; Raasch et al. (1997) Society for Neuroscience Abstracts 23). These findings demonstrate that a considerable level of motor learning capability persists in relation to the impaired arm. We also have evidence that chronic stroke subjects are able to use the residual motor learning capability to partially regain functional elbow/shoulder torque combinations (for example, shoulder abduction/external rotation combined with elbow extension) during an eight-week training protocol (see Ellis et al. (2002a) Program No. 169.2 Abstract Viewer/Itinerary Planner. Washington, D.C.: Society for Neuroscience Abstracts; Ellis et al. (2002b) Neurology Report 26: 191, Abstract; and Ellis et al. (2003) Program No. 714 Abstract Viewer/Itinerary Planner. Washington, D.C.: Society for Neuroscience Abstracts).

The Use of Robotics in Stroke-rehabilitation

At present, very little technology exists to support the recovery phase of stroke rehabilitation. However, there has been a surge of academic research on this topic in recent years (see, for example, Proceedings of the ICORR International Conference on Rehabilitation Robotics, 2001 and 2005). Of the academic research in progress, most research centers have elected to attempt to adapt or re-configure industrial robots for use in this application (Lum et al. (1995) Arch. Phys. Med. Rehabil. 83: 952–959). While this appears to be a reasonable approach it suffers from a critical drawback: twenty years of experience with industrial robots has shown that low impedance comparable to the human arm cannot be achieved with these machines. Because of their electromechanical design and control architecture, commercial robots are intrinsically position-controlled machines that do not yield easily under the action of external forces. Active force feedback can be used to enhance robot responsiveness but it is not sufficient to produce the "back-drivability" (low mechanical impedance) required to move smoothly and rapidly in compliance with a patient's actions (Lawrence (1988) Proc. IEEE Int. Conf. Robotics & Automation 1185–1191).

In contrast to commercial robotic technology, the MIT-MANUS robotic device was specifically designed for clinical neurological applications (Hogan et al. (1995) J. Interactive Robotic Therapist). The MIT-MANUS robotic device is configured for safe, stable and compliant operation in close physical contact with humans. Its computer impedance control (synonymous with position control) system modulates the way the robot reacts to mechanical perturbation from a patient or clinician and ensures a gentle compliant behavior (technically, a low and controllable impedance) (Hogan (1985) ASME J. Dynamic Systems Measurement and Control 107: 1–24). Operationally, a low impedance means that the robot can "get out of the way" as needed. However, due to the impedance control system, there is a moderate level of resistance due to inertia that the user must overcome to produce movement. This attribute limits the applicability of the MIT-MANUS to subjects who are able to exert enough force to overcome the inertial resistance of the device.

To test the feasibility of robot-aided neuro-rehabilitation, MIT investigators have used the MIT-MANUS robotic device in pilot studies on a daily basis for over seven years with CVA (cerebral vascular incidence resulting in a stroke), Parkinson's disease, multiple sclerosis, spinal cord injury, amyotrophic lateral sclerosis (ALS), and Guillain-Barré (GB) patients at the Burke Rehabilitation Hospital. The key research objective in these pilot studies was to validate the concept of robot-aided exercise therapy and assess whether: (a) robot-aided therapy had adverse effects, (b) patients would tolerate the procedure, and (c) manipulation of the impaired limb influenced motor recovery. The results in these pilot clinical trials with 96 stroke patients showed that robot-aided neuro-rehabilitation did not impede recovery or exacerbate joint or tendon pain, and no adverse events occurred in an estimated 2000 hours of operation involving close contact with patients. A questionnaire administered during the bi-weekly standard assessment by the therapists showed that robot-assisted therapy was well accepted and tolerated by the patients. Most important, results indicated that patients in the experimental group improved further and faster, outranking the control group in the clinical assessments of the motor impairment involving shoulder and elbow. (See, for example, Aisen et al. (1997) Arch. Neurol. 54: 443–446; Krebs et al. (1998) IEEE Transact. Rehab. Engineer. 6: 75–87; Krebs et al. (2000) VA J. Rehab. Res. Dev. 37: 639–652; Volpe et al. (2001) Curr. Opin. Neurol. 14: 745–752; Volpe et al. (2000) Neurology 54: 1938–1944, and Ibid. (1999) Neurology 53: 1874–1876). However, a shortcoming of the MIT-MANUS obviating its usefulness for application in the evaluation and rehabilitation of gravity-induced discoordination is that it only works in a horizontal plane unable to provide various levels of limb support or operate in all directions of movement. In addition, impedance control technology must use a very light structure which may contain mechanical shortcomings such as friction or mechanical compliance. Even though forces may be measured at the patient interface, no compensation can be made for such non-linearities since they occur between the force control device, the motor, and the patient introducing errors that cannot be compensated.

Several similar US Patents have been issued to the above technology. For example, U.S. Pat. No. 5,466,213 to Hogan et al. is directed to an interactive robotic therapist that guides a patient's limb along a desired path through a desired series of exercises. The robotic therapist incorporates sensors that provide position, velocity, and force information at the patient's hand. The reference, however, does not teach using-force and position information in both real and virtual environments to measure, treat, or self-rehabilitate impaired movement performance.

U.S. Pat. No. 5,421,798 to Bond et al. is directed to an apparatus for evaluation of a limb of a test subject. The distal end of the limb is secured to the apparatus. The test subject moves the limb along a linear track. At least two components of the forces generated by the limb against the track are sensed. The force components are used to calculate the forces applied at each limb joint contributing to movement. The reference, however, does not teach using force and position information in both real and virtual environments to measure, treat, or self-rehabilitate impaired movement performance.

U.S. Pat. No. 5,830,160 to Reinkensmeyer is directed to a movement guiding system for quantifying, diagnosing, and treating impaired movement performance. The guiding system guides movement of a limb along a linear path and can quantify movement performance by measurting constrqaint forces generated during the movement. The reference does not teach force and position information in both real and virtual environments to measure, treat, or self-rehabilitate impaired movement performance.

U.S. Pat. No. 6,413,190 to Wood and Koval is directed to a rehabilitation apparatus and method that monitors patient rehabilitation thaearapy activity, the apparatus detecting sequential muscle contractions thereby operating a computer game that reflects the movement upon a screen. The patient is therefore encouraged to ensure that two muscles move in a temporal sequence to "play" the game. The reference does not teach using force and position information in both real and virtual environments to measure, treat, or self-rehabilitate impaired movement performance.

U.S. Pat. No. 4,936,299 to Erlandson discloses a rehabilitation apparatus having a robotic arm controlled by application software and a control board of a CPU. The patent also discloses a viewing screen and that the rehabilitation is initiated and under direction of a therapist. The reference does not teach using force and position information in both real and virtual environments to measure, treat, or self-rehabilitate impaired movement performance.

U.S. Pat. No. 6,613,000 to Reinkensmeyer discloses a system providing arm movement therapy for patients with sensory motor impairments having a joystick controlled by application software of a CPU over the World Wide Web using client-side applets. The patent also discloses a viewing screen and that the rehabilitation is performed without the direction or supervision of a therapist but in response to a predetermined desired therapeutic exercise. The reference does not teach using force and position information in both real and virtual environments to measure, treat, or self-rehabilitate impaired movement performance.

Admittance control technology uses a force measurement device (loadcell) placed at the patient interface. The loadcell functions as the force feedback device in a closed loop force control system. Therefore the forces are always controlled at the patient's interface, and system non-linearities mentioned before are minimized because they occur inside the force control loop and can therefore be compensated to a large degree.

A commercial robot that uses admittance control is the HAPTICMASTER (HM) from FCS Control Systems. The FCS Control Systems' control technology originated and was patented in the late 1970s in the field of flight training and simulation to generate aircraft control forces for the pilot. It has matured over the years from a patented to a company proprietary technology. See U.S. Pat. No. 4,398,889, herein incorporated by reference in its entirety.

The HAPTICMASTER, which was designed with rehabilitation applications in mind, has low inertia such that the user doesn't feel much resistance when attempting to move the device. The low level inertial properties of the HM enable application to individuals with all levels of impairment severity including individuals with severe impairment who would otherwise be unable to move against the inertial resistance of other robotic devices. Work done at the University of Reading, England has shown that the robot is safe and can assist reaching movements to various targets in the workspace of the paretic arm following stroke (Coote and Stokes (2003) Technol. Disabil. 15: 27–34; Harwin and Hillman (2003) Robotica 21; Marinncek et al (2001) Association for the Advancement of Assistive Technology in Europe AAATE '01. Amsterdam; Washington, D.C.: IOS Press,). However, it has been employed to assist subjects in reaching movements with the upper extremity constantly supported by an external device.

Each of the robotic devices described above demonstrate the ability to use robotics as a device for implementing therapeutic training post-stroke. In addition, each of these devices is capable of measuring motion and tracking progress during training. With this current patent, we propose to generate virtual mechanical/visual environments that can simulate weightlessness or make the body or limb progressively heavier to beyond its actual weight. Using these realistic simulated environments generated by a combination of multi degree of freedom robotics and visual feedback we can measure the effect of abnormal joint torque coupling in the upper and lower extremities as well as train individuals to slowly relearn to deal with the weight of their limb or body while reaching (arm) or walking (leg).

Virtual Reality

Haptics is the science of applying tactile or force sensation to human interaction with computers. A haptic device is one that involves physical contact between the computer and the-user, usually through an input/output device, such as a joystick or data gloves, that senses the body's movements. By using haptic devices, the user can not only feed information to the computer but can receive information from the computer in the form of a felt sensation on some part of the body. This is referred to as a haptic interface. For example, in a virtual reality environment, a user can pick up a virtual tennis ball using a data glove. The computer senses the movement and moves the virtual ball on the display. However, because of the nature of a haptic interface, the user will feel the tennis ball in his hand through tactile sensations that the computer sends through the data glove, mimicking the feel of the tennis ball in the user's hand. Typical uses a haptic interface are disclosed in U.S. Pat. No. 6,636,161 (Rosenberg, issued Oct. 21, 2003) and U.S. Pat. No. 6,697,043 (Shahoian, issued Feb. 24, 2004).

BRIEF DESCRIPTION OF THE INVENTION

The invention provides a system and methods to measure, to train and/or to assist and/or to rehabilitate and/or self-rehabilitate an individual having a neurological condition that results in loss in the ability to coactivate certain muscle combinations in affected limb or similar extremety of the individual.

In one embodiment the invention provides a method for measuring, treating, and self-rehabilitating an individual having a neurological condition, the method comprising: (i) providing a system comprising mechanical means, at least one computer, display means, and interconnecting means, the mechanical means further comprising an interacting instrumented member that interacts with the body or a part thereof of the individual, a force sensor, a force generator, at least one moveable non-compliant linkage, and a base, the force sensor further being attachedly connected by the linkage to the force generator, the linkage having at least three degrees of freedom, the computer further comprising an interactive software program, and the base supporting at least one of the above; (ii) securing a body or part thereof of the individual to the interacting instrumented member; (iii) permitting the individual to move the body or part thereof to a desired position; (iv) sensing the force required to move the body or part thereof using the force sensor; (v) producing force input data using the sensed force; (vi) transmitting the force input data from the force sensor to the computer; (vii) processing the force input data using the interactive software program; (viii) transmitting the processed data to the display means whereby the display shows a virtual environment; (ix) processing the data to produce force output data; (x) transmitting the force output data to the force generator and the linkage thereby generating a force upon the interacting instrumented member and the body or part thereof, the resulting generated force upon the body or part thereof causing the muscles and nerves in the body or part thereof to be stimulated, the stimulation resulting in regaining muscle coactivation patterns and associated joint torques patterns for the individual; thereby measuring, treating, and self-rehabilitating the individual. In a preferred embodiment the neurological condition is selected from the group consisting of hemiparetic stroke, cerebral palsy, head trauma, and multiple sclerosis. In a more preferred embodiment the neurological condition results in a loss of independent joint control in the body or part thereof.

In one embodiment the body or part thereof is selected from the group consisting of a whole body, a trunk, a shoulder, a neck, a head, an arm, an elbow, a wrist, a hand, a hip, a leg, a knee, an ankle, and a foot.

In another embodiment the interconnecting means provide radio communicating signals, electrical communicating signals, photonic communicating signals, or a combination thereof, between the mechanical means, the computing means, and the display means.

In another embodiment the force generator is an actuator selected from the group consisting of a rotary hydraulic motor, a linear hydraulic motor, a pneumatic motor, and an electric motor.

In yet another embodiment the method further comprises the step of attaching at least one position measurement device, the position measurement device being placed on a predetermined position selected from the group consisting of an end effector, a linkage, a force sensor, a force generator, a shoulder, a hip, a neck, and a head.

In a still further embodiment the generated force compensates for the force due to gravity on the body or part thereof and wherein the generated force is equivalent in magnitude to between about −1 times and about +4 times the force of gravity upon the body or part thereof.

In another embodiment the generated force is essentially equivalent to a force required for manipulating joint abduction torques of the individual, the joint selected from the group consisting of the shoulder and the hip.

In another embodiment the interacting instrumented member further comprises a sensor selected from the group consisting of a force sensor, a position sensor, and a motion sensor.

In an alternativel embdiment the system further comprises an end effector articulatedly attached between the appendage attaching member and the force generator.

In another alternative embodiment the method further comprises a step of determining the position of the appendage attaching member to generate position data and providing the position data to the computer and the display.

In still another alternative embodiment the method further comprises the computer further comprising memory means for storing the force input data, the virtual environment, the position data, and the force output data.

In another embodiment the interacting instrumented member further comprises an electrical stimulator, the electrical stimulator being further releasably connected to an extremity of the body or part thereof. In a preferred embodiment the electrical stimulator stimulates movement in the extremity of the appendage, the extremity being selected from the group consisting of a finger, a thumb, a hand, an elbow, a shoulder, a wrist, a toe, a foot, an ankle, a knee, and a hip. In a more preferred embodiment the stimulated movement results in a propriosensory effect in the individual. In a most preferred embodiment the stimulated movement results in a dermal tactile sensory effect or muscle sensory effect in the individual. In another alternative embodiment the interacting instrumented member comprises a member selected from the group consisting of a splint, a limb support, a hand support, a foot support, and a force-sensing treadmill.

In another embodiment, the invention provides a system for providing at least one force in at least one plane to a limb or extremety of an individual having a neurological condition, the force resulting in negating the force acting upon the limb or extremety due to gravity and allowing the individual to move the limb or extremety in a desired direction, the system comprising means for supporting the limb or extremety, a device for detecting the force of gravity acting upon the limb or extremety, and a device for negating the force of gravity acting upon the limb or extremety. In one embodiment, the system is a haptic system. In another embodiement, the force further results in allowing the individual to move the limb or extremety to a target site. In a preferred embodiment, the force is provided in at least two planes. In a more preferred embodiment, the force is provided in at least three planes. In another preferred embodiment, the force is provided in a plurality of planes.

In another embodiment, the system comprises a device for negating the force of gravity acting upon the limb or extremety having at least one degree of freedom. In another embodiment the device for negating the force of gravity acting upon the limb or extremety has at least one degree of freedom. In preferred embodiment the device for negating the force of gravity acting upon the limb or extremety has at least two degrees of freedom. In a more preferred embodiment, the device for negating the force of gravity acting upon the limb or extremety has at least three degrees of freedom. In a most preferred embodiment, the device for negating the force of gravity acting upon the limb or extremety has at least four degrees of freedom.

The invention also provides a system as recited above further comprising means for supporting the individual, the means selected from the group consisting of a chair, a bed, a back support, and a trunk support.

The invention also provides a system as recited above wherein the device for detecting the force of gravity acting upon the limb or extremety further comprises a power transfer medium coupled at one end to the device for detecting the force of gravity acting upon the limb or extremety and extending away from the system to a second end coupled to a computer prossesor.

The invention also provides a system as recited above wherein the device for negating the force of gravity acting upon the limb or extremety further comprises a power transfer medium coupled at one end to the device for negating the force of gravity acting upon the limb or extremety and extending away from the system to a second end coupled to a computer prossesor.

In one other embodiment, the system as recited above further comprises a device for detecting the force of gravity acting upon the limb or extremety and/or a device for negating the force of gravity acting upon the limb or extremety wherein the device is automated.

The invention also provides a method of training an individual having a neurological condition using the system as recited above. In one embodiment, the training results in the individual having improved motor neuron activity compared with the motor neuron activity prior to the training, the method of training comprising the steps of: (i) providing a system that provides at least one force in at least one plane to a limb or extremety of an individual having a neurological condition, the force resulting in negating the force acting upon the limb or extremety due to gravity and allowing the individual to move the limb or extremety in a desired direction, the system comprising means for supporting the limb or extremety, a device for detecting the force of gravity acting upon the limb or extremety, and a device for negating the force of gravity acting upon the limb or extremety; (ii) supporting a limb or extremety of the individual using the means for supporting; (iii) requiring the individual to move the limb or extremety to a target site; (iv) repeating step (iii) ten times; (v) repeating step (iv) three times; (vi) repeating step (v) to a different target; (vii) repeating step (vi) three times; (viii) allowing the individual to rest for a predetermined time period; (ix) repeating the cycle of steps (ii) through (viii) but concomitantly increasing the negating force acting upon the limb or extremety by about 10% of that used in the previous cycle of steps; (x) repeating step (ix) at least twenty two times; the steps resulting in training the individual having improved motor neuron acitivity when the negating force acting upon the limb or extremety is equivalent to about 300% of the weight of the individual's limb or extremety.

In a further embodiment, the invention provides a robotic device, the robotic device comprising a support splint, the support splint communicably attached to a force sensor, the force sensor communicably attached to a transducer capable of transducing a force input into a corresponding electrical or optical output; a central processing unit communicably attached to and receiving an input signal from the transducer and further communicably attached to and sending an output signal to a motor, wherein the motor is functionally attached to the robot arm.

In one embodiment, the system is a haptic system. In another embodiment, the force further results in allowing the individual to move the limb or extremety to a target site. In a preferred embodiment, the force is provided in at least two planes. In a more preferred embodiment, the force is provided in at least three planes. In another preferred embodiment, the force is provided in a plurality of planes.

In another embodiment, the invention provides a robotic device, the robotic device comprising a support splint, the support splint comprising an arm rest, an arm cuff, a hand splint; a gimbal, a strain gauge force sensor, an end effector, a robot arm, a robot stand, and a servo motor; wherein the support splint is fixedly attached to the gimbal, the gimbal is fixedly attached to the strain gauge force sensor, the strain gauge force sensor is attached to the end effector, and the end effector is fixedly attached to the robot arm; the robot arm is fixedly attached to the servo motor, and the servo motor is fixedly attached to the robot base; wherein in use, when a first force is applied to the support splint the force is then transmitted to the gimbal, then transmitted to the strain gauge force sensor, the strain gauge force sensor converts the first force into a proportional electronic signal, the electronic signal is transmitted to a control unit comprising a central processing unit, the central processing unit processes the electronic signal, the central processing unit transmitts the processed electronic signal to the servo servo motor, and the servo motor responds to the electronic signal by exerting a second force upon the robot arm. Preferably, the second force acting upon the robot arm results in an apparent inertial mass of the robot arm at the gimbal of not more than 2 kg. More preferably, the apparent inertial mass of the robot arm at the gimbal is not more than 1 kg.

In an additional embodiment, the gimbal has at least two degrees of freedom. More preferably, the gimbal has at least three degrees of freedom. In a further additional embodiment, the load cell has at least three degrees of freedom. More preferably, the load cell has six degrees of freedom.

In a yet further embodiment, the gimbal comprises at least one position sensor. The position sensor is used to measure the elbow and shoulder rotation angles. Preferably the gimbal has a three position sensor, a position sensor for each degree of freedom.

In a further embodiment of the invention, the robotic device further comprises supporting means, the supporting means selected from the group consisting of a chair, a bed, a back support, and a trunk support. In one preferred embodiment of the invention, the robotic device comprises a chair. In a more prefered embodiment, the chair is a Biodex chair. In a still further embodiment the robotic device further comprises a T-support track, wherein the robotic device and the chair are positioned proximally on the T-support track.

In an additonal embodiment of the invention, the robotic device comprises a visual display unit (VDU) screen in interactive communication with the control unit. The interactive communcation is preferably a signal, the signal being selected from the group cnsisting of an electrical signal, a photonic signal, and a radio signal.

In another embodiment, the robotic device comprises a data acquisition computer with screen and printer that is in communication with and regulates the robotic device and the three-dimensional (3-D) visual display screen. In a preferred embodiment, the computer comprises the user interface to allow data collection during the evaluation and training of the stroke subject and subsequent data access for creating standardized clinical progress reports.

In one embodiment of the invention the robotic device, the control unit comprises a computer with a real-time operating system, motor amplifiers, and an emergency circuit.

In another preferred embodiment, the robotic device comprises safety and protection mechanisms to safeguard against equipment malfunction. In an additional embodiment, the robotic device comprises hardware safeguards to physically limit the available robot travel range. In a preferred embodiment, a disconnecting switch is activated when a predetermined and safe force level at the subject's arm is exceeded, while simultaneously turning electrical power off to the robotic device.

The invention provides a method for diagnosing a neurological condition in a subject, the method comprising measuring a subject's joint torques using the robotic device as described herein. In a preferred embodiment, the neurological condition is selected from the group consisting of hemiparetic stroke, cerebral palsy, head trauma, and multiple sclerosis.

The invention also provides a method for measuring the degree of rehabilitation of a subject with a neurological condition, the method comprising measuring a subject's joint torques at a first time starting rehabilitation and then periodically during rehabilitation using the robotic device as described herein. In a preferred embodiment, the neurological condition is selected from the group consisting of hemiparetic stroke, cerebral palsy, head trauma, and multiple sclerosis.

The invention also provides a method for measuring the temporal change in severity of a neurological condition in a subject, the method comprising measuring a subject's joint torques at a first time and then periodically over time using the robotic device as described herein. In a preferred embodiment, the neurological condition is selected from the group consisting of hemiparetic stroke, cerebral palsy, head trauma, and multiple sclerosis.

The invention provides a method for treating a neurological condition in a subject, the method comprising training a subject using the robotic device as described herein, the treatment being tracked and assessed by measuring the subject's isometric joint torques. In a preferred embodiment, the neurological condition is selected from the group consisting of hemiparetic stroke, cerebral palsy, head trauma, and multiple sclerosis.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 illustrates exemplary elements of the system.

FIG. 2 illustrates an exemplary embodiment of the system further comprising computing means that can interact with the gravity sensing means and the gravity negating means.

FIG. 3 illustrates an alternative exemplary embodiment of the system.

FIG. 4 shows a schematic diagram of a common model for the admittance control algorithm of the system.

FIG. 17 illustrates another embodiment of the system of the invention showing the robotic device and the chair, the robotic device comprising a scissor mechanism to provide the degrees of freedom.

DESCRIPTION OF THE INVENTION AND PREFERRED EMBODIMENTS

Figure 5:
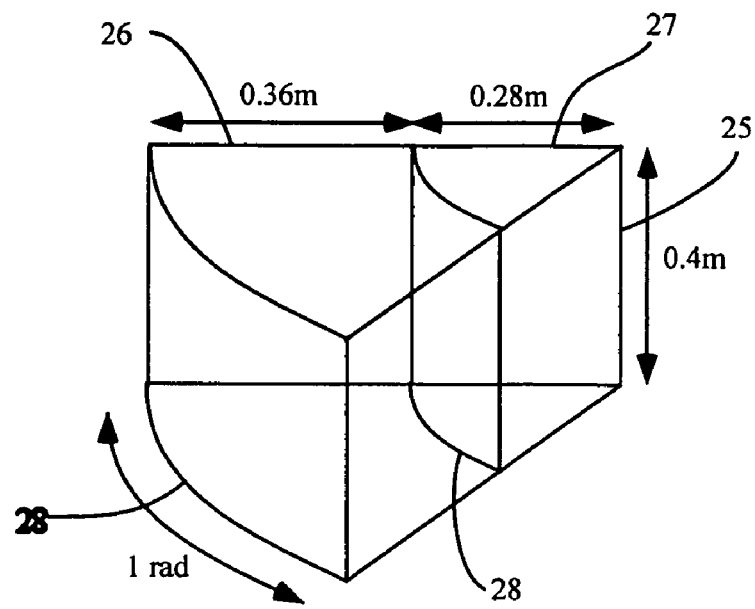
FIG. 5 shows exemplary dimensions of the volumetric workspace accommodated by the system in use.

The invention provides provides a method and a system having means for allowing a subject having a neurological condition, such as hemiparetic stroke, cerebral palsy, head trauma, a motor neuron disorder, or multiple sclerosis, to use a limb or other appendage, such as an arm, a leg, a hand, a finger, a thumb, or the like, and to provide a training and rehabilitation system and method that can regenerate the subject's abitlity to perform tasks unaided or with little additional energy input.

The method and system can be used to support such an individual's whole body or part thereof, such as the trunk, the shoulder, the neck, the head, the arm, the elbow, the wrist, the hand, the hip, the leg, the knee, the ankle, and the foot. One object of the invention is to controllably apply a force to the body or body part such that the body or body part has a sensation of weightlessness. Under these force conditions the individual responds more quickly to training and self-rehabilitation than an individual using a system from the prior art. Such an improvement is of particular benefit in relation to time spent in rehabilitation, thereby reducing clinical and health-releated costs, and from a physiological perspective to a more rapid rehabilitation of tissue that might otherwise become wasted through lack of use or lack of stimulation. In particular, the method and system help the joint abduction responses thatare of consequence for arm extension, walking, and the like.

The system comprises means to support the limb or appendage of an individual, the means being, for example, a splint, a plate, a glove, a sock, a boot, or the like; means for detecting the force of gravity upon the limb or appendage, the means being, for example, a force sensor or the like; means for negating the force of gravity upon the limb or appendage, the means being, for example, a linear actuator, a rotary actuator, or the like; controlling means for integrating the output from the force detecting means and the input to the force negating means, the means being, for example, an integrated circuit, a switch, a microprocessor, a linear actuator, a lever arm coupling, or the like.

The means for negating the force of gravity can have at least one degree of freedom; for example, a solenoid has one degree of freedom, the Arm Coordination Training 3D device disclosed below has at least threedegrees of freedom in which the force is controlled and three degrees of freedom in which the position is measured. The invention does not limit the number of such means that can be used in combination with one another, nor limit the use of combining different such means in one system.

The system of the invention solves the problem that when the arm is extended away from the shoulder and body of a user, the force of gravity acting upon the extremity in proportion to the distance of the extremety (wrist or hand) to the axis of the shoulder, thereby activating the abnormal synergy between shoulder abduction and elbow flexion. The user therefore experiences less resistance to extending his or her arm and is more able to reach a distant object. The system therefore has the novelty of manipulating the force of gravity upon a limb or appendage of a subject.

The method and system can also have incorporated parameters that determine velocity of movement and range of force necessary to aid treatment and self-rehabilitation using the disclosed elements of the invention. Such parameters are, for example, but not limited to, a subject's condition, such as being adult or child, being a victim of stroke, a victim of head trauma, a child having cerebral palsy, degree of disability, size, age, time elapsed since onset of condition, or the like. Additional parameters can include, but are not limited to, configuration of the system, such as being mounted upon a floor, wherein the subject sits or stands in proximity to the system, whether the system is mounted as an exoskeleton that the subject wears, sits or stands in, or is mounted on a wheelchair or the like, or a chair, bed, stool, or the like, or is mounted on a separate object, such as a workstation, a control panel, a cockpit, a capsule, or the like, or is mounted in a garb that a subject can wear, such as a diving suit, a space suit, or the like.

Figure 18:
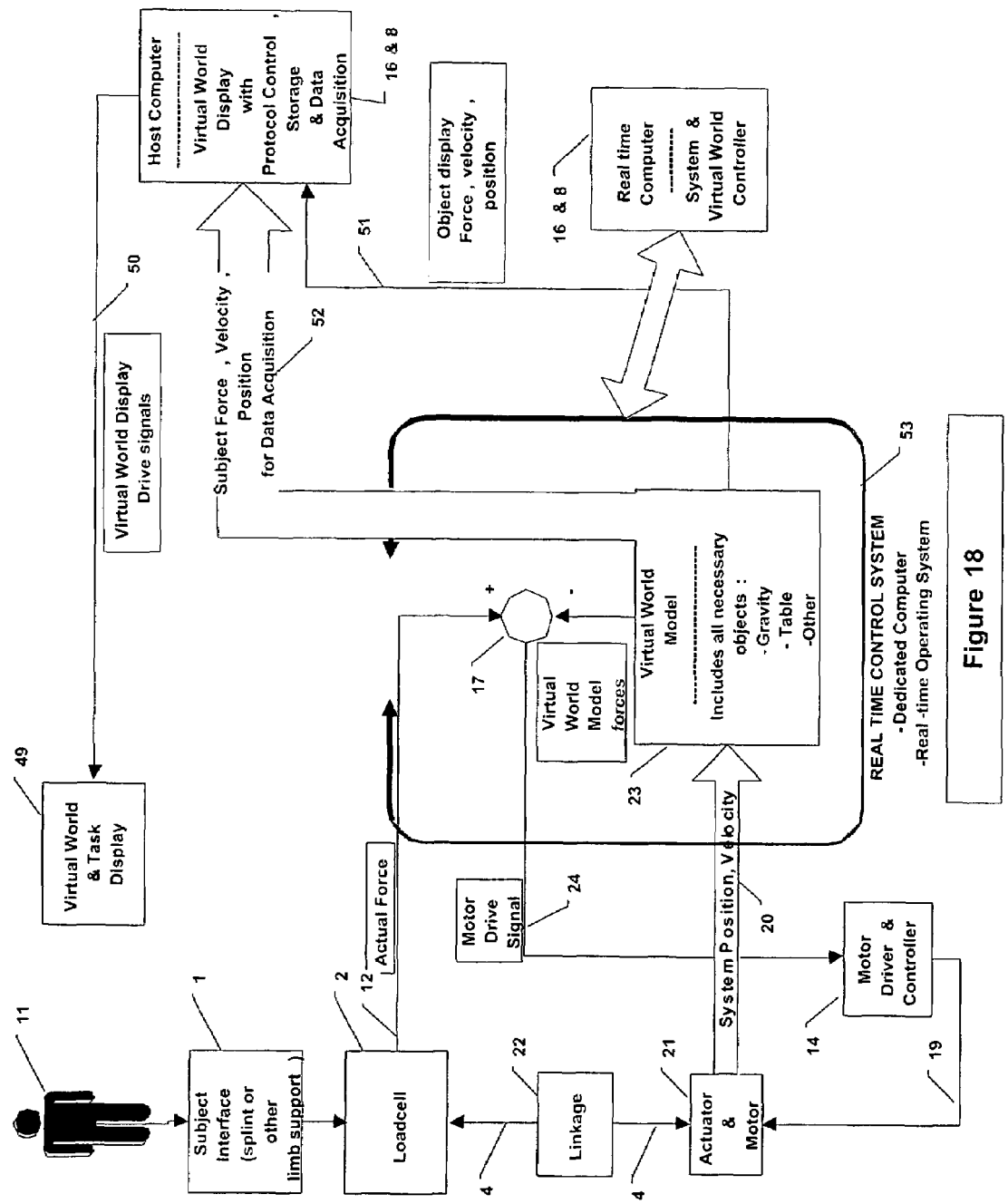
FIG. 18 illustrates a schematic diagram of elements of the invention.
Figure 19:
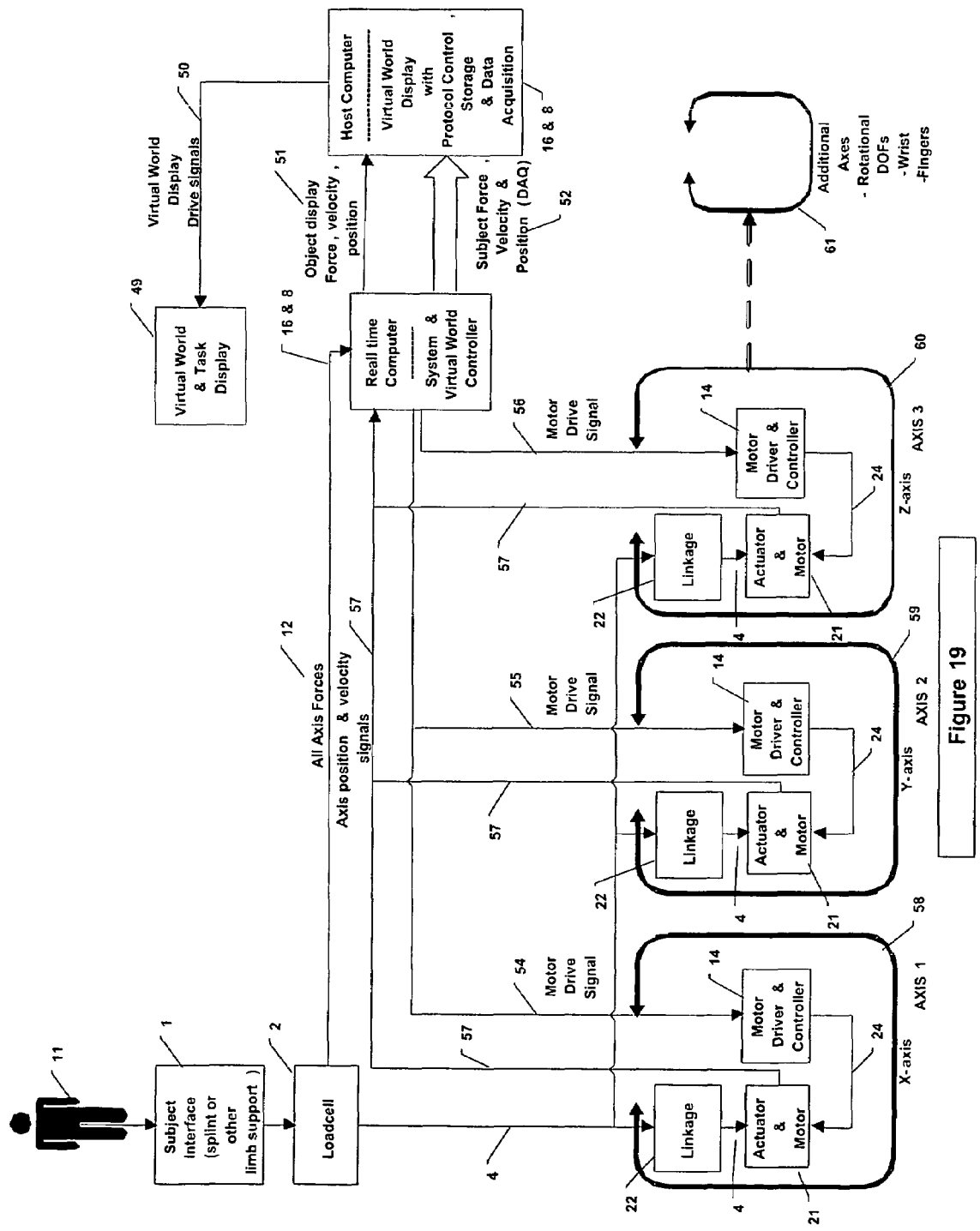
FIG. 19 illustrates a schematic diagram of alternative elements of the invention having at least three degrees of freedom.

Two exemplary schematic illustrations of the system are shown in FIG. 18 and FIG. 19.

The development of the Arm Coordination Training 3D device ($ACT^{3D}$) to measure gravity-induced discoordination and to deliver highly controlled patient-specific upper extremity rehabilitation provides a superior training and quantification tool that will benefit individuals who have had a stroke. Likewise, administering novel functionally relevant training protocols to a chronic stroke population whom has reached a functional plateau in formal physical therapy may demonstrate that these individuals retain untapped potential for recovery not reached prior to discharge from outpatient therapies.

Isometric Training to Reduce Gravity-induced Discoordination

We have trained stroke subjects to generate isometric joint torques that explore combinations away from the abnormal torque patterns they exhibit (Ellis et al. (2002a) supra; Ellis et al. (2002b) supra; Ellis et al. (2003) supra). More specifically we combined shoulder abduction and elbow extension torques as one of the isometric strengthening tasks that stroke subjects performed. After an eight-week training protocol (three 1.5 hour sessions per week) the ability to concurrently generate shoulder abduction with elbow extension and shoulder flexion improved. In all chronic stroke subjects (n=8) trained to date we saw marked improvements in the ability to combine elbow extension torques (normalized to max abilities) and shoulder abduction torques (expressed as a function of arm weight). To demonstrate the effect of these improvements on reaching movements, we compared the pre- versus post-training kinematic results for our most impaired subject trained to date. Before the training period this stroke subject was not able to reach a gray target when actively supporting the arm against gravity. Following the eight-week isometric training protocol he was able to reach the target. Moreover, he was able to reach the target with a velocity profile similar to the one obtained with his arm on an air bearing support at the onset of the training. Thus our subject significantly increased his reaching ability both with regards to reaching area and movement velocity.

In the less impaired subjects the improvements during reaching movements were not always as consistent. We believe that this is due to the fact that these subjects were already able to extend their elbow when lifting up their arm against gravity. However, this ability may be challenged when subjects attempt to move objects with a certain weight especially during reaching movements. This expectation is based on our observation that even mildly impaired subjects exhibit abnormal isometric torque patterns when generating maximum shoulder abduction torques (Dewald and Beer (2001b) Topics Stroke Rehab. 8: 1–11). The use of the robotic device of the invention for the administration of a selective dynamic strengthening protocol tests this hypothesis by having subjects lift loads greater than the weight of their arm, simulating tasks such as picking up a book. Under these conditions we saw similar reductions in work area occurring in these more mildly impaired stroke subjects.

The lower extremeties have also been evaluated using the disclosed isometric protocols and have produced similar results thereby validating the method and system for the whole body. Therefore all references herein to upper extremeties can also be taken to apply to the lower extremeties.

Thus, there is a current deficiency in rehabilitation science calling for a device that can both accurately evaluate and deliver highly controlled patient-specific upper extremity rehabilitation while taking into account disabling nature of shoulder elbow joint torque coupling when attempting to lift the limb against the force due to gravity. The present invention realizes this need by providing high-resolution measurements of physiological (strength and coordination) and functional (reaching workspace) performance at various levels of limb support and in various virtual environments. The device, accessories, and methods described herein allow practitioners to evaluate and train movements with partial limb support, and hence vastly increase the ability to successfully train subjects across all levels of impairment. Furthermore, the invention is based upon results from an isometric training study. The advantages of the invention is that it incorporates the ability to control the level of limb support and to move in a three-dimensional (3-D) workspace, features that are unavailable in the isometric training protocol or in other robotic technologies. Therefore, it is expected that the device and method of the invention have clear potential to improve the functional abilities in the upper limb by reducing the gravity-induced discoordination during real-world reaching efforts beyond that of isometric training.

The invention is designed to deliver novel interventions that train and rehabilitate individuals with a broad spectrum of upper extremity reaching impairment to progressively overcome the negative effects of gravity by providing various levels of limb support. Furthermore, the device and methods of the invention emulate real life scenarios such as reaching and retrieval of objects of different weight in space. The device interfaces with the user in a safe and comfortable fashion quickly setup by a healthcare provider. It may be implemented with the large number of people who currently suffer from the disabling effects of stroke.

The major focus of the invention is that it implements a virtual mechanical environment both to evaluate synergistic movement constraints and to deliver patient-specific rehabilitation for the impaired limb with gravity-induced discoordination. Furthermore, in an effort to accommodate patients with various severities of impairment, the invention is able to simulate: 1) movements of objects with increasing mass for mildly impaired subjects, 2) movements with partial support of the impaired limb for the more severely impaired subjects and 3) movements in both horizontal and inclined planes. The overall goal of the invention is to increase the paretic arm's functional workspace by increasing levels of shoulder abduction while reaching in various directions. This is accomplished by having subjects perform reaching movements to targets on virtual planes centered through the shoulder progressively from down to horizontal to up. It is important to note that it is simpler to measure the forces acting upon and position of a subject's limb having the system mounted on an exo-skeleton than if the subject is not contrained. Constraining the shoulders is therefore necessary in situations whereby the system would otherwise enable the subject to move the shoulder in relation to the body and arm, thereby confounding the ability of the system to accurately measure force, position, and acceleration.

In one embodiment of the invention, a 3-D force controlled robot arm was implemented to progressively overcome the negative effects of gravity (abducting or lifting the weight of impaired limb) during functional movements. In this embodiment, the robotic device comprises a controlled robot arm that is a modified HAPTICMASTER device (FCS Control Systems B.V., Schiphol, The Netherlands). The device integrated a 3-D force controlled robot arm with a seating system and a compact real-time two-dimensional (2-D) or 3-D virtual reality visual system, creating an upper extremity rehabilitation device that implements a virtual mechanical environment for the progressive reduction of upper extremity gravity-induced dysfunction. The seating system and the robot arm were placed on a T-support track that allowed the seating system and the robot to move relative to each other and to rotate (see, for example, U.S. Pat. No. 5,209,223).

Admittance Control Robotics

Admittance control technology uses a force measurement device (loadcell) placed at the patient interface. The loadcell functions as the force feedback device in a closed loop force control system. Therefore the forces are always controlled at the patient's interface, and system non-linearities mentioned before are minimized because they occur inside the force control loop and can therefore be compensated to a large degree.

One feature of the robot arm is that it must have virtually no inertia such that the user does not feel any resistance when attempting to move the device. The inertia of the robot arm should not be more than 2 kg. Currently, the only commercially available robot that couples this feature with a 3-dimensional operational capability is the HAPTICMASTER device (FCS Control Systems), but other robots with these features may also be used. The low level inertial properties of the HAPTICMASTER device enables application to individuals with all levels of impairment severity including individuals with severe impairment who would otherwise be unable to move against the inertial resistance of other robotic devices. Work done at the University of Reading, England has shown that the robot is safe and can assist reaching movements to various targets in the workspace of the paretic arm following stroke (Coote and Stokes (2003) Technol. Disability 15: 27–34; Harwin and Hillman (2003) Robotica 21; and in: "Assistive technology-added value to the quality of life": AAATE '01. Amsterdam, Association for the Advancement of Assistive Technology in Europe, vol. 10 (2001) Marincek, Bühler, Knops and Andrich, editors, Washington, D.C.: IOS Press, Washington D.C.). However, it has not been employed to assist subjects in reaching movements with the upper extremity constantly supported by an external device.

A modified HAPTICMASTER was used in the ACT$^{3D}$ system prototype as described in the Examples section to demonstrate and validate the systems and protocols envisioned, even though the HAPTICMASTER's range of motion is limited, but adequate for protocol validation. The robot can be redesigned such that individuals will be able to move over virtual planes in all dimensions of their available reaching area, albeit limited in travel. Furthermore, the actual limb movement and level of limb support in a virtual mechanical environment can be provided via real-time 3-D visual feedback, such that individuals can learn to progressively support more of the weight of their arm as they reach for objects on various horizontal and vertical planes. To date no center applying robotic technology has targeted the negative effects of gravity loading on reaching with the impaired upper limb in all planes of available movement.

The type of admittance control (force control) that is used in the robotic device results in a device that individuals can move freely as if they were not attached to the robot. The key features accomplished with this type of control system are that the weight of the robot itself and any friction in the movement are compensated and thus not sensed by the user. These properties are considered when designing a device for rehabilitation, especially for individuals with stroke who will exhibit weakness and discoordination as compared to able-bodied individuals.

In a preferred embodiment of the present invention, the robotic device is designed to support a subject's arm and is configured such that the subject can move their arm over virtual planes in all dimensions of their available reaching area. Furthermore, the actual limb movement and level of limb support in a virtual mechanical environment are provided via real-time 3-D visual feedback, such that subjects can learn to progressively support more of the weight of their arm as they reach for objects on various horizontal and vertical planes.

The robotic device can comprise a transducer that converts the force input to an output signal comprising an electrical signal, an optical signal, a radio signal, or combination thereof. The output signal is transmitted to the computer unit that receives the output signal for processing and which then sends the processed output signal to the servo motor.

The visual display unit may be of any suitable type, for example, with respect to the 3-D visual display, the Dimension Technologies Inc. (DTI, Rochester N.Y.) 18.1" screen is preferred for the following reasons: it does not require consumers to wear glasses and when the screen is centered, it provides realistic real-time 3-D displays of the virtual arm, targets and objects. Furthermore, the screen also permits for regular 2-D displays as well without losing its resolution. Any display having similar properties can be used with the invention, such as a 19" LCD VDU from Dell (Round Rock, Tex.).

The primary application of the invention is to test a patient's ability to generate shoulder abduction torque while the paretic arm is moved over virtual planes. However, it is also feasible to monitor the ability of stroke survivors to control wrist and finger extension using a commercially available pressure mapping system installed on the hand splint. Individuals with stroke would be asked to extend their fingers and wrist (zero pressure) while performing the same reaching motions toward a virtual object. The force exerted by the fingers and the palm of the hand on the splint can be measured by the pressure mapping system and displayed for feedback.

Another example of the application of the invention is the addition of neuromuscular electrical stimulation of hand and wrist muscles as subjects get close to objects that they would like to grasp in their virtual world. This is particularly helpful if volitional control of finger, wrist and/or elbow extensors is absent or insufficient.

With respect to therapeutic techniques various approaches can be used based under the unifying principle of multi-degree of freedom strengthening. Although in all cases movements on virtual planes will be encouraged, while generating increasing levels of shoulder abduction, the strengthening of shoulder/elbow flexion/extension torques, required especially for reaching directions can be accomplished by different approaches: 1) ballistic movements; 2) movements in viscous fields or 3) movements with capped maximum velocities or isokinetic movements.

In another embodiment, the device includes a data acquisition computer with screen and printer wherein the computer is in communication with and regulates the robot and the 3-D DTI screen. In a preferred embodiment, the computer houses the user interface to allow data collection during the evaluation and training of the stroke subject and subsequent data access for creating standardized clinical progress reports. A large segment of chronic and acute patients could benefit from the proposed 3-D measurement and training system. It is important to point out that currently there are no commercially available systems designed for rehabilitation of the upper extremity. All systems that have been reported in the literature are currently being tested as research units and cannot deal with the devastating effects of abnormal elbow/shoulder synergies on movement following stroke. As such, this is the first unit that targets the devastating effects of synergies when lifting the paretic arm against gravity.

In a preferred embodiment, safety and protection mechanisms are implemented to safeguard against equipment malfunction, which could cause an axis to move at high speed towards an extreme position. Software limits for travel, velocity, acceleration, and force, incorporated in the real time software continuously guard against inadvertent signals in the robot control systems, and once triggered, turn the electrical power off to the robot in a controlled manner, thereby forcing the robot in a passive state. Over and above these software safeguards, hardware safeguards can also be included to physically limit the available robot travel range. These travel limits can be set by the health care provider, dependent on the available and safe range of motion of the patient so as not to cause any harm to the patient under the most severe equipment malfunction, an uncontrolled motor run-away. A "quick disconnect" can also be introduced at the patient/machine interface. In a preferred embodiment, this disconnect activates when a predetermined and safe force level at the patient's arm is exceeded, while simultaneously turning electrical power off to the robot.

Hardware

Figure 6:
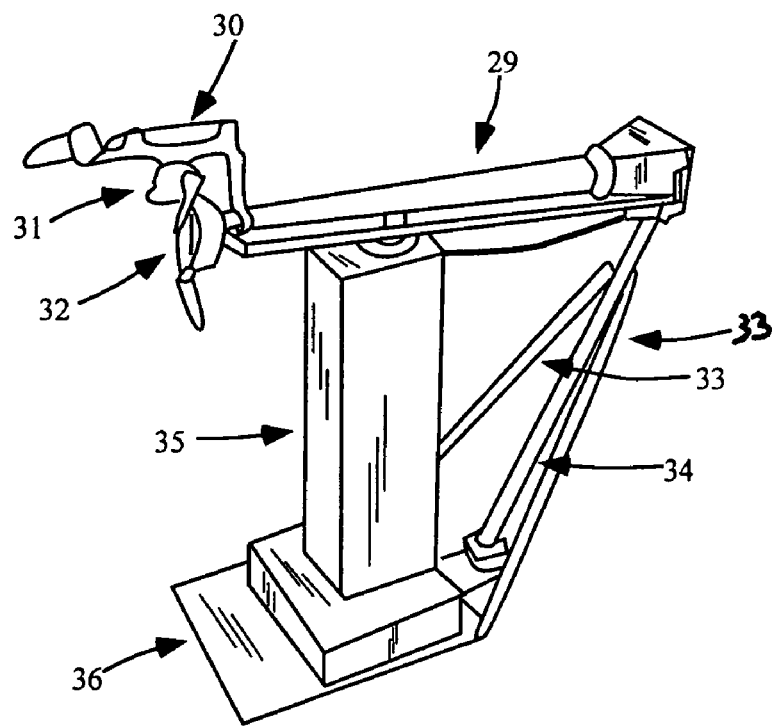
FIG. 6 illustrates an exemplary prototypic embodiment of the haptic system, the haptic system being a robotic device.
Figure 15:
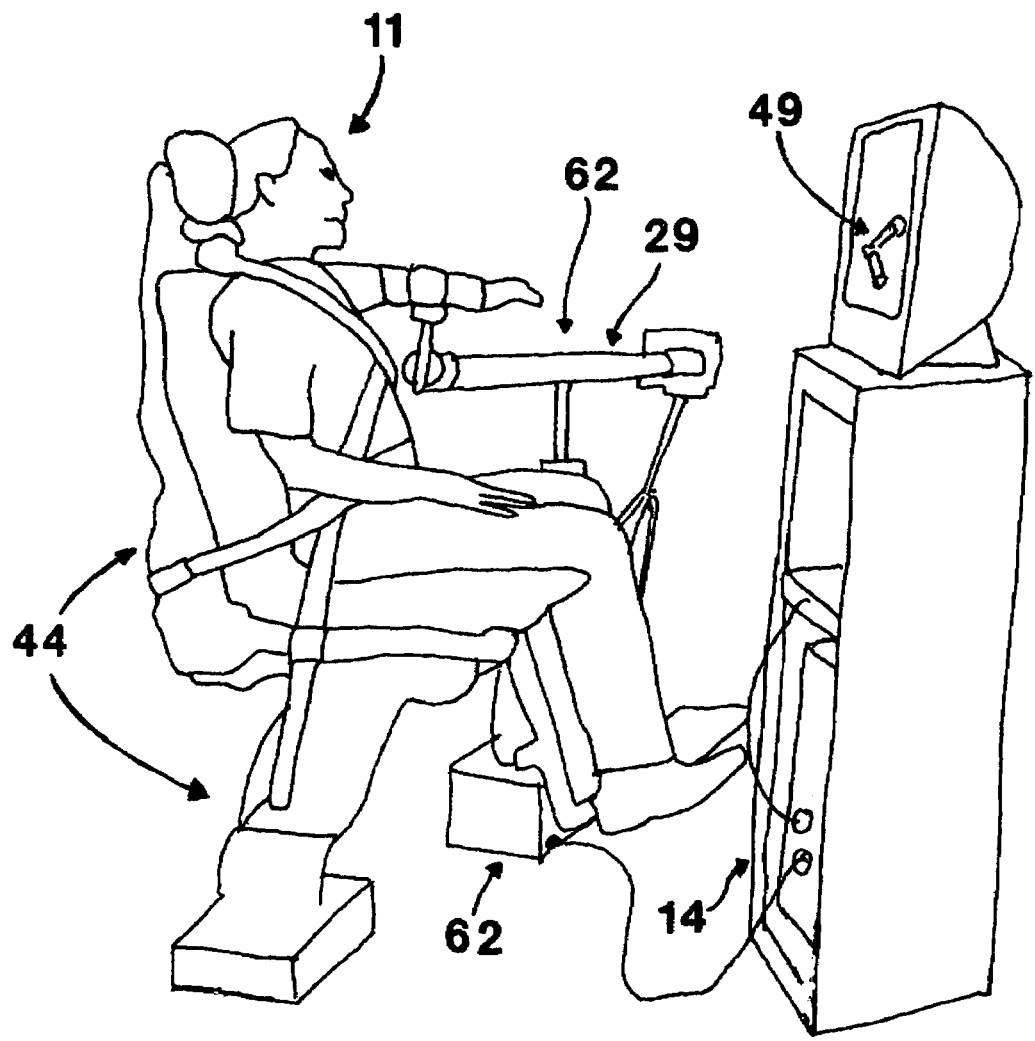
FIG. 15 illustrates one embodiment of the system of the invention showing the robotic device, the chair, and the visual display unit. In particular the robotic device illustrated is a 3-DOF haptic device with independent degrees of freedom.
Figure 16:
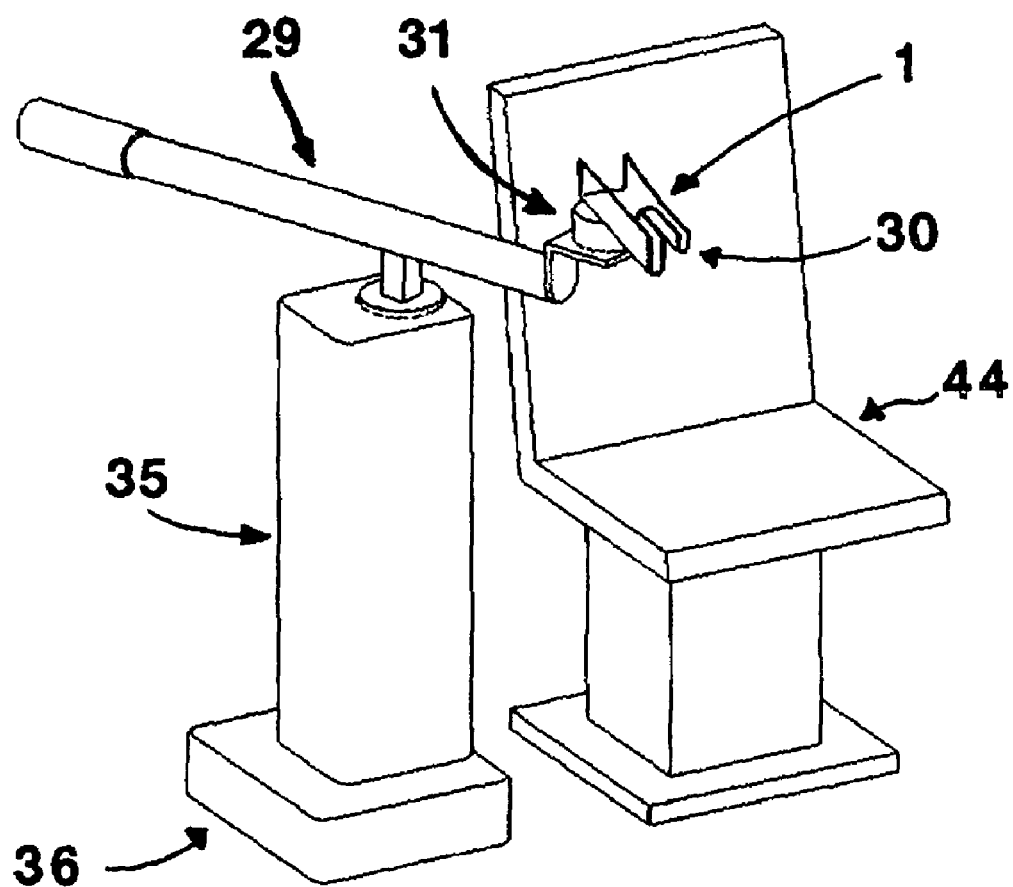
FIG. 16 illustrates one embodiment of the system of the invention showing the robotic device and the chair.
Figure 17A:
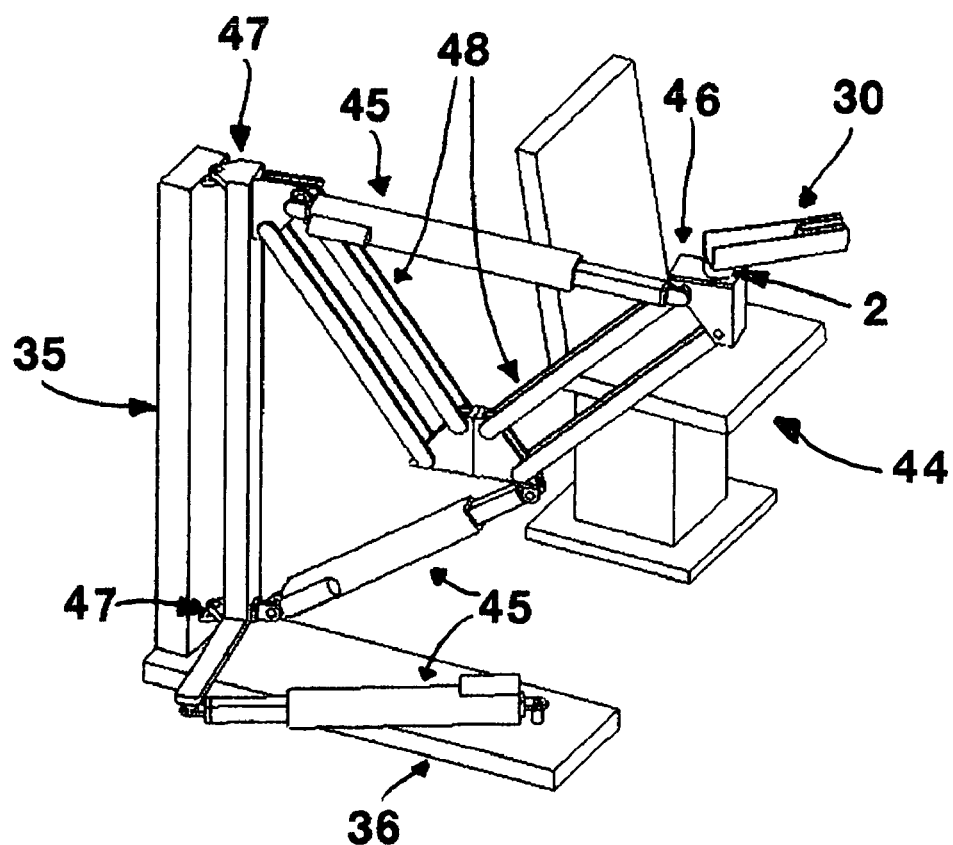
FIG. 17A shows the device from a three-quarter view.
Figure 17B:
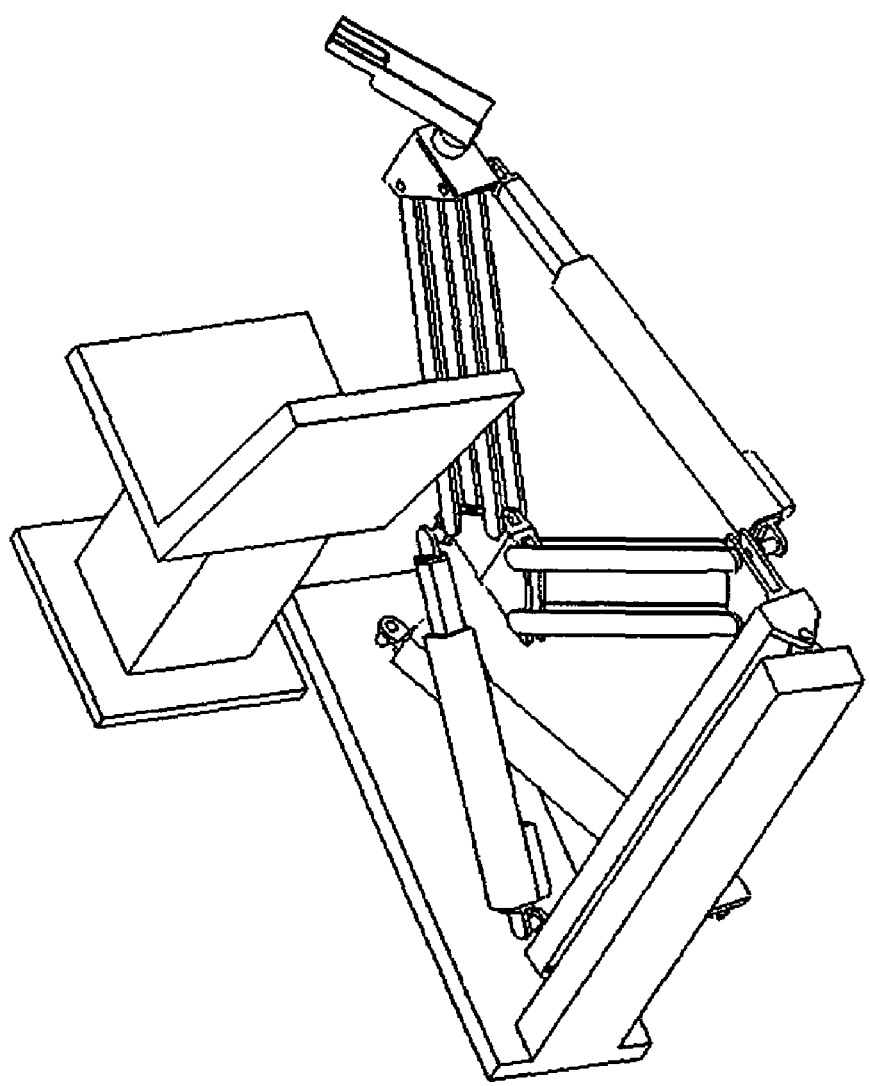
FIG. 17B shows the device from a top view.

The HAPTICMASTER hardware comprises two main functional components: the robot arm (29) and the control unit (14), shown in FIG. 6 and FIG. 15. The robot arm serves as the actual force display unit, whereas the control unit houses the electronics such as amplifiers, safety relay, and the haptic server.

The robot arm is built with zero backlash and minimal weight in consideration of the human operator. Zero backlash is a requirement because human tactile senses have a spatial resolution of vibrations with amplitudes as small as 10–100 microns, such as those caused by play in mechanical parts (Burdea (1996) "Force and Touch Feedback for Virtual Reality" Wiley, New York N.Y.). Minimal weight is necessary for safety, as both the speed and the mass of the robot arm determine its energy content in a possible collision with the human operator. The speed is set to the value of a normal human arm motion (for example, about 2.2 m/s), and light-weight aluminum tubing construction minimizes the mass of the robot arm. The kinematic chain from the bottom up yields: base rotation, arm up/down, arm in/out, which gives three degrees of freedom at the end effector. A volumetric workspace is created, which is large enough to enclose most human single-handed or double-handed tasks, shown in FIG. 5. The dimensions of the volumetric workspace space are approximately as follows: horizontal rotational displacement: about 1 rad; vertical displacement: about 0.4 m (15.7"); and horizontal extent: about 0.36 m (14.2"). In the alternative, the dimensions can be about 1 rad, about 0.4 m, and about 0.18 m (7.1"), respectively. In another alternative, the dimensions can be about 0.5 rad, about 0.2 m (7.85"), and about 0.18 m, respectively. In yet another alternative, the dimensions can be from between 0.5 rad and 1.0 rad, 0.2 m and 0.4 m, and 0.18 and 0.36 m, respectively.

The support splint can be provided in sizes suitable to conform and fit the anatomical size of a subject's hand, wrist, and/or arm.

Anti-backlash leadscrew spindles are mounted with a flexible coupling to the axis of a DC brushed motor, such as the Starsys Precision Brush Motor (Starsys Research Corporation, Boulder, Colo.). This backlash-free solution introduces some friction in the mechanism. However, the friction is completely eliminated by the control loop, up to the accuracy of the force sensor. The result in force control mode is a backlash-free, stick-free, and slip-free smooth motion at the end effector. A sensitive strain gauge force sensor is located right behind the end effector. Such strain gauge force sensors, (or load cells) are well known in the art, for example, the JR3 Sensors, the EBB Series Load Cell, or the LSP Series Load Cell, available from Transducer Techniques (Temecula, Calif.). By placing the force sensor adjacent to the end effector, the interaction force is measured as close to the human hand as possible to avoid distortion of the force signal and to optimize system performance. Exchangeable end effectors can be mounted to the force sensor to match the application.

Servo motors that drive the robot arm are well known to those in the art, and include, for example but are not limited to, the 815 BR or the 1525-BRS (Servo Dynamics Corp., Chatsworth, Calif.).

The control box contains electronics such as the computer, motor amplifiers, and an emergency circuit. The virtual model is rendered by a dedicated computer with a real-time operating system, such as VxWorks (Wind River Systems, Alameda Calif.), QNX, LynxOS, VRTX, pSOS, Windows-CE, Nucleus RTX, RT Linux, or the like, herein termed the haptic server. Such servers and operating systems are well known to those in the art. It runs at a fixed 2,500 Hz refresh rate. This frequency is high enough to guarantee a haptic quality for a smooth and realistic experience since it is approximately ten times higher than the maximal human discrepancy value (Burdea G. (1996) "Force and Touch Feedback for Virtual Reality" Wiley, New York, N.Y.). Finally, the PID motor control loop runs on the amplifiers at a 20 kHz pulse width modulated frequency.

Figure 7:
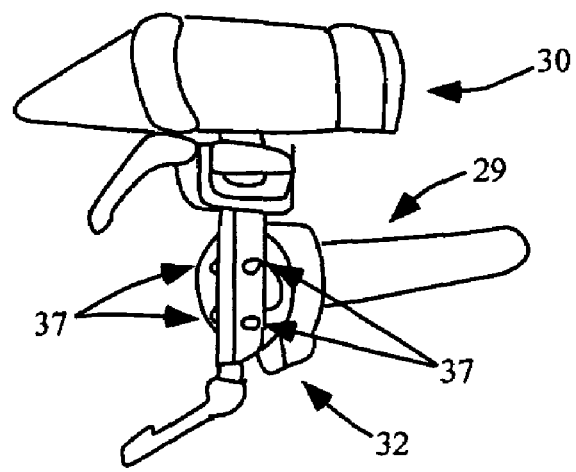
FIG. 7 shows a partial view of a part of the prototypic robotic device comprising the support splint, the gimbal, position sensors, the strain gauge force sensor, and the robot arm.

It must be noted that other configurations of the haptics device are possible. FIG. 7 shows one such example of a 3-D haptic device concept where the axes are fully independent. It is expected that many versions of the haptics device can be developed, accommodating the full performance envelope of force, velocity and position.

It is understood that for someone skilled in machine design arts many different ways can be found to drive an end effector in three or more degrees of freedom. Another example which is far more complex is a Stewart platform given in FIG. 8. This is used extensively in flight simulators to provide motion sensation to the pilots. The hexapod structure uses six actuators, and is thus capable of providing 6-DOF motion. In the system of the present invention the end effector and associated additional hardware may be mounted on the top platform.

End effectors may also be of different configurations dependent on the application and type. As mentioned before; specific protocols integrating wrist and/or hand functions may require unique and dedicated end effectors.

At least one position measurement device can be included in the system, a position measurment device such as a tracker, a potentiometer, or the like. The position measurement device can be fixedlyattached to any part of the system, however it is preferable to attach the position measurement device to or adjacent to a joint, a sensor, or the like so that the position of an element of the system can be accurately determined. In addition, several position measurement devices can be attached to different locations on the system in order to obtain an accurate estimate of the position of the entire system.

Extra-skeletal Approach

In addition to end effector approaches, extra-skeletal robots can be designed to implement the same virtual mechanical environment to overcome gravity-induced dysfunction in upper extremity paresis following stroke, head trauma and spastic cerebral palsy. As long as such systems can provide the means to alter weight of the limb in the workspace of the arm and the ability to provide resistance to motion, if so desired, the neurorehabilitation concept discussed as part of this application can be realized.

Rehabilitation Software and Visual System

The rehabilitation software can allow for data collection of evaluation and training data. The quantitative evaluation software is developed to:

A: Determine any limitations in available torque combinations by performing ballistic reaching/retrieval arm movements in different directions while maintaining various levels of shoulder abduction torque. The protocol allows an operator to establish the severity of abnormal coupling(s) between shoulder/elbow torques as a function of limb support activity. The software can display sparks and/or provide a sound (indicating that the arm is touching the table) if subjects do not maintain an abduction level within 10% of the assigned torque value during reaching/retrieval movements.

B: Determine the maximal reaching workspace. Similar movements as in A) can be performed for different inclination angles of the virtual table to determine the maximal reaching workspace of the paretic arm. In the case that subjects are mildly impaired, the weight of the arm can be increased by simulating objects with increasing weight. The software can be developed to provide a quantitative measure of workspace for different percentages of active limb support.

The results provided by protocols A & B can be used to establish parameters for the training software. The software for the training protocols is similar to the software developed for the quantification and evaluation protocols allowing visual display and measurement of virtual planar surfaces and active support of the limb. In addition, this software can allow for a progressive increase of active support of the limb during subsequent training sessions.

An additional component in the training software can be to provide a subject the ability to strengthen the paretic limb while subjects move on a virtual plane supporting part of the weight of the arm. This can be realized by:

A) Ballistic reaching movements using predetermined targets on the virtual plane;

B) Reaching motions within an imposed viscous field on the virtual plane; and/or C) Isokinetic reaching motions that limit the maximum movement velocity on the virtual plane.

The training software can include these options for research and clinical trials.

It is expected that the software may evolve into a stimulating "gaming scenario", perhaps associated with some form of "scoring" providing the subject with additional incentives. This is even more important if the subjects are children reorienting the concentration from the rehabilitation aspects to more "fun and games".

Figure 9:
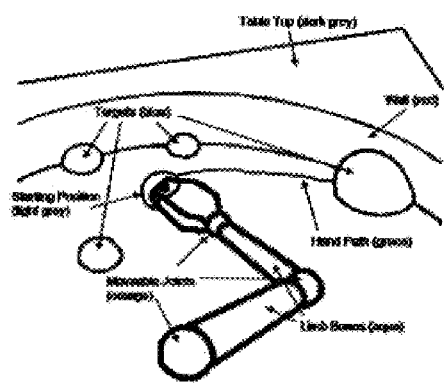
FIG. 9 shows a 3-D visual feedback display.

In order to create a realistic training environment for individuals with stroke, 3-D visual feedback is incorporated into the system. We have used a 3-D virtual reality world displayed on a large flat panel monitor, as is seen in FIG. 9. The display includes an avatar of the subject's arm and hand providing a direct link from the task to the virtual world. FIG. 9, an exemplary display of a VDU screen image, shows a virtual environment comprising a surface (table-top; dark grey), the area delimited by the reach of the individual's arm (wall; red), several targets in the vicinity if the individual's reach (hemispheres; blue), an avatar of the individual's virtual arm consisting of movable joints (hand, elbow, and shoulder, orange) and limb bones (forearm and upper arm; blue-green), the starting position of the hand (hemisphere; light grey), and the track/path of the hand to one of the targets (lines; green). Different colors may be chosen to represent different objects or avatars in the display according to the subject's preference. Subjects with color-blindness may also have a choice of color schemes.

User Interface Software

With an application programming interface (API), the user creates the virtual model on the haptic server. The real-time operating system on the haptic server interprets the virtual model and generates the trajectories for the robot, based on the force sensor input. The haptic server also incorporates issues like safety guards, communication protocols, and collision detection with virtual objects. In one embodiment, the HAPTICAPI, which is a C++ programming interface, is used by the programmer to define or modify the virtua haptic world via an Ethernet connection to the robot that controls the internal state machine (FCS Control Systems). Through the robotic control, haptic effects can be created (like dampers and springs), and spatial geometric primitives can be defined (like spheres, cones and cubes). Simple virtual worlds can be created using these effects and primitives. When more complex virtual worlds are required, e.g. with meshed surfaces or deformation, another rendering method needs to be applied. A local mass model will be rendered on the haptic server, and the forces acting on this mass due to interaction with the virtual world are rendered from a host computer. When the end effector collides with a virtual object, an appropriate force and displacement are presented to the user. The relationship between force and displacement is given by the object properties of the virtual model (for example, stiffness, damping, friction, or the like). With a penalty-based method, the appropriate relation between force and displacement is calculated by the real-time operating system and incorporated in the position, velocity, and acceleration signal.

Control Algorithm

The robot uses an admittance control algorithm. A force sensor measures the interaction force between the user and the system. From these forces, a virtual mass model calculates position, velocity, and acceleration (PVA), which an object touched in the virtual world would obtain as a result of the applied force. An example of such an admittance control algorithm is currently used and available in FCS Control Systems' devices (see U.S. Pat. No. 4,398,889 herein incorporated by reference in its entirety).

The virtual world defines the space in which the object lives (for example, gravity, environmental friction, position of the object, etc.) and the object properties (for example, mass, stiffness, damping, friction, etc.). The virtual mass model will typically contain a mass larger than zero, to avoid commanding infinite accelerations and causing system instabilities. The PVA-vector serves as a reference signal for the robot, realized by a PID servo control servo loop.

With proper feedback gain settings, this control loop will compensate the real mass of the manipulator up to a factor of six, and terminates its internal friction up to the accuracy of the force sensor. So, if the mass of the manipulator behind the actuator is 15 kg, the operator feels only 2.5 kg at the end effector.

Since gravity can also be almost eliminated, the perception of the user is that they are moving a mass much less than 2.5 kg. The admittance control algorithm is shown in FIG. 4.

Robot Control Software

The robot control software allows specification of the following features from the user interface:

a) Inclination angle of the virtual table imposed by the robot arm, which can be varied while exercising the paretic limb.

b) Virtual environment imposed by the robot: the environment can be made to feel like a hard constraint onto a plane, allowing no movement above or below it with free or guided motion on that plane; or like a one-sided upper or lower constraint. These abilities will allow individuals with stroke to lift their arm from the virtual table with or without a downward "virtual gravity" force and away from the virtual surface.

c) Virtual objects: generation of mechanical effects when manipulating a virtual object on the plane or addition of the "virtual gravity" force when a subject attempts to lift and move objects of different weights. See U.S. Pat. No. 4,398,889 incorporated herein by reference in its entirety.

Training

Following an injury to the brain, gravity introduces limitations to a compromised system and restricts arm movements in stereotypical ways. These limitations are associated with the activation of anti-gravity shoulder muscles used to lift the arm, and associated overflow into elbow/wrist and hand flexor muscle activation. This in turn reduces elbow extension capabilities, because it is necessary to overpower the flexion activation in order to reach outward away from the body. Furthermore, flexor activity in the wrist and hand are expected to increase as well resulting in very disabled upper limb. The phenomena of synergies (shoulder abduction involuntarily coupled with elbow/wrist and finger flexion) is seen in a variety of cases of brain injury; it has been most extensively studied in adult hemiparetic stroke, but it is also seen in cerebral palsy (CP) and head trauma. Using a state-of-the-art haptic system such as, but not limited to, the current ACT 3D robot prototype or the like, can investigate how subjects are able to interact in an environment of reduced or eliminated gravity, as well as enhanced gravity. Such a system can be used to provide infinite support via haptically rendered rigid objects, or to provide forces along the vertical axis scaled to a subject's limb weight. In this way, the system is able to reduce or increase the amount of abduction torque a subject is required to create at the shoulder in order to work in the environment. Using an instrumented arm rest and adjustable gimbal on the end effector of such a system, finger/wrist/elbow/shoulder angles (kinematics) and forces/moments (kinetics) can be monitored during movement. Finally, the system may also include a supporting means, such as, but not limited to, a chair, a bed, a back support, and a trunk support, that will constrain movements of the trunk during the monitoring/therapy of arm movements. Furthermore, such a supporting means should have various adjustable and marked degrees of freedom that will allow the experimenter/therapist to place a test subject in the same position for subsequent measurement/therapy sessions.

We disclose herein that even highly impaired subjects are able to increase available workspace of the hand when gravity and the need to activate anti-gravity muscles are eliminated. Similarly, mildly impaired subjects may revert to similar patterns when required to work in environments of enhanced gravity, where they are required to generate abduction torques greater than that to lift the weight of their own limb. These patterns and movement characteristics as well as their treatment are elucidated using a variety of protocols, as described by example below.

Reaching in a plane can be explored with the system of the invention while concurrently measuring shoulder/elbow/wrist and finger forces and torques. This allows back calculation of shoulder and elbow torques as well as wrist and finger forces/torques, which is a highly relevant output measure of the system. The system should also allow for the monitoring of higher speed movements during which subjects will be able to perform ballistic reaches in several conditions: fully supported by a rigid plane passing though the center of rotation of the shoulder, and with various levels of support that virtually reduce or enhance gravity.

To reduce the impact that hyperexcitable stretch reflexes (or spasticity) may also have on the compromised arm, a second protocol emphasizes slow movements. Subjects are asked to slowly make the largest circle they can with their arm. Like the ballistic reaching protocol, this is done under rigid support from a haptic table, or while the subject is concurrently producing particular levels of active limb support. By reducing the impact of spasticity, the best picture of available work area can be constructed.

A third way that the device can be used is to characterize free reaching that is not confined to a plane. By unlocking the position of the gimbal and removing rigid haptic constraints, a subject's freely selected path can be studied. The effects of gravity can still be studied in the same manner by applying bias forces at the end effecter, as in previous protocol descriptions. This method removes external constraints and restrictions and provides a potentially more relevant look at movement following brain injury.

A fourth ability that the haptic system should have is to allow for the introduction of particular fields and external perturbations to the arm. Such a system can then be used to investigate the effect anti-gravity muscle activity on the expression of spasticity. The system can be used to provide a quick constant acceleration perturbation to the elbow joint, shoulder joint, or a combination of the two. Using system analysis techniques and information obtained from EMGs, excitability of the reflex can be elicited and compared to the level of active limb support requirements.

A fifth property of the system is that it should be able to measure kinetics of the wrist and fingers during the monitoring of the effect of gravity on reaching and retrieval motions with the arm.

Finally, viscous fields can be implemented to the system during all or parts of the movement to induce velocity dependent resistance against movement. This may allow us to more fully characterize the movement patterns of more mildly impaired subjects.

These protocols, or combinations thereof, can be used as outcome measures for the intervention protocols described in the next section, or as a means of more specifically quantifying impairments that result from the presence of gravity and need to drive activation of shoulder abduction/external rotation muscles.

Under the guidance of our gravity-induced discoordination concept as disclosed above, several therapeutic intervention protocols can be realized. A protocol in which gravity is progressively re-introduced during outward reaching over a period of 8 weeks can be used. Training can be further extended or shortened according to a subject's clinical needs. More specifically, subjects can be trained to reach outward towards virtually displayed targets that are situated on a horizontal plane associated with the height of the shoulder. Progressive gravity re-introduction training can be expanded beyond reaching on a shoulder-height horizontal plane to three-dimensional or free reaching. Such a protocol would include reaching toward outward targets positioned on the three dimensional surface defined by the most distant reaching points throughout the entire volume of the arm's range of motion. Gravity could be progressively re-introduced as in the previous protocol over a period of time as a subject is trained to reach outward toward randomized targets in their three-dimensional work area.

Figure 13:
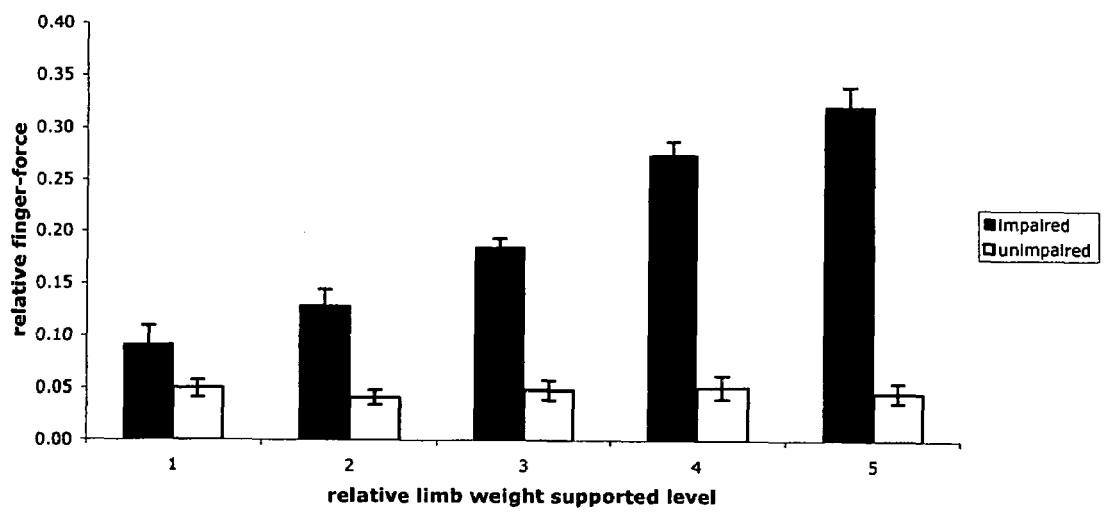
FIG. 13 illustrates data for relative finger flexion forces for increasing levels of active limb support.
Figure 14:
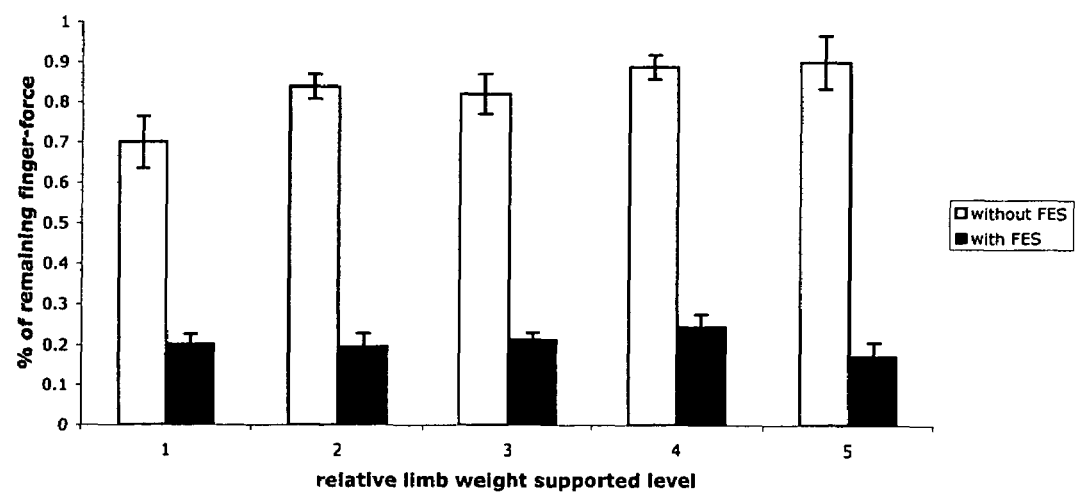
FIG. 14 illustrates the percent of finger extension force that subjects were able to generate with and without assistance of functional electrical stimulation (FES) of wrist and finger extensor muscles.

The acquisition of targets during progressive gravity re-introduction training can also be expanded upon by integrating functional electrical stimulation (FES) of the elbow, wrist, and finger extensors during antigravity reaching and subsequent grasping of virtual objects. In the absence of FES subjects progressive generate greater finger and wrist flexion forces when lifting up more of the weight of their arm (see FIG. 13). Artificial stimulation of extensors would assist in counteracting abnormal flexor activity that occurs during reaching toward targets in the presence of gravity (FIG. 14). This assistance may facilitate the changes resultant from progressive gravity re-introduction by triggering appropriate muscle activity.

Progressive gravity re-introduction training during horizontal and free reaching with and without functional electrical stimulation can also be employed in the presence of horizontal viscous fields, inertial fields simulating the transport of objects, or controlled joint angular velocities (isokinetic reaching). The implementation of these various forms of horizontal resistance against the direction of reaching would have a strengthening effect that may facilitate the changes resultant from progressive gravity re-introduction.

LIST OF REFERENCE NUMERALS

1. Means for supporting limb
2. Device for detecting force of gravity (force sensor; load cell)
3. Device for negating force of gravity (force generator; actuator)

4. Means for interdispositioning and communicating between detecting device and negating device
5. Support
6. Means for articulating and attaching system to a support
7. Basal substrate (floor, table, etc.)
8. Means for computer processing
9. Power transfer medium
10. Power transfer medium
11. User, subject, or individual
12. Force transducer
13. Force sensor
14. Controller
15. Power transducer
16. Integrated circuit
17. Power transducer
18. Virtual mass
19. Power transducer to servo motor
20. Power transducer to virtual world (virtual environement)
21. Servo motor
22. Force transducer
23. Virtual world (virtual environment)
24. Power transducer
25. Vertical axis of motion
26. Horizontal axis of motion
27. Horizontal axis of motion, unused
28. Rotational arc of motion
29. Robot arm
30. Splint
31. Gimbal
32. JR3 force sensor
33. Dampers
34. Spline
35. Robot base
36. Bottom plate
37. Position sensor
38. Top or mobile plate
39. Upper leg
40. Cylindrical joint
41. Lower leg
42. Lower universal joint
43. Fixed base plate
44. Chair
45. Actuator
46. End effector
47. Y-axis hinge
48. Linkage
49. Display
50. Virtual world display signals
51. Object display (FVP)
52. Subject force, velocity, and position for data acquisition
53. Real time control system (dedicated computer; real time operating system)
54. Motor drive, X-axis
55. Motor drive, Y-axis
56. Motor drive, Z-axis
57. Axis position and velocity signals
58. Axis 1
59. Axis 2
60. Axis 3
61. Additional axes (rotational DOFs; wrist, fingers)
62. Robotic device

EXAMPLES

The invention will be more readily understood by reference to the following examples, which are included merely for purposes of illustration of certain aspects and embodiments of the present invention and not as limitations.

Example I

Modification of the HAPTICMASTER to Meet Required Specifications

The required needs for stroke subjects fall well within the performance criteria of the current version of the HAPTICMASTER. Its peak force ability of 250 N is considerably greater then the maximum adduction forces measured in our strongest stroke subjects (Dewald and Beer (2001a) Muscle Nerve 24: 273–283). The position resolution of the HAPTICMASTER device was approximately 4–14 µm. This was more than sufficient for the kinematic measurements needed for the real time visual display (see also rehabilitation software development). The maximum deceleration (50 m/s$^2$) and simulated stiffness (50,000 N/m) were also more than sufficient for the mechanical environments we intend to simulate. The only performance criteria that was adjusted was the maximum velocity of the robot which was originally 1.4 m/s, less than the needed 2.25 m/s to accommodate the peak tangential velocities seen at the forearm and upper arm during ballistic movements in mildly impaired subjects (Beer et al. (2004) Exp. Brain Res. 156: 458–470). The HAPTICMASTER device was redesigned to accommodate these movement velocities. The basic drive mechanisms of the three primary axes were modified to accommodate the new requirements. This was accomplished by selecting a different drive motor, in this case a brush type servo motor, or by changing the force transmission consisting of a lead screw, or a combination thereof. The lead crews were placed such that one screw was directly connected to a drive motor and this combination is used to drive one axis. Since there are three axes there are also three motor/lead screw combinations. Drive motor and lead screw changes can affect the output torque and speed of each axis. This makes it possible to select a combination of motor and lead screw suitable to the requirements of each of the three axes.

Example II

Impairment Quantification

Reaching in a plane was explored using the system while concurrently measuring shoulder/elbow/wrist and finger forces and torques. This allowed back calculation of shoulder and elbow torques as well as wrist and finger forces/torques, which is a highly relevant output measure of the system. The system also allowed for the monitoring of higher speed movements during which subjects were able to perform ballistic reaches in several conditions: fully supported by a rigid plane passing though the center of rotation of the shoulder, and with various levels of support that virtually reduce or enhance gravity. Subjects were asked to move to a variety of targets within a plane that passes through the center of rotation of the shoulder. These targets encompass both reach and retrieval directions, and the plane can be horizontal, inclined or declined. In this way, the ACT$_{3D}$ system can characterize fast point to point movements in several aspects of the total work volume while also monitoring wrist and finger kinetics and/or kinematics.

Figure 10A:
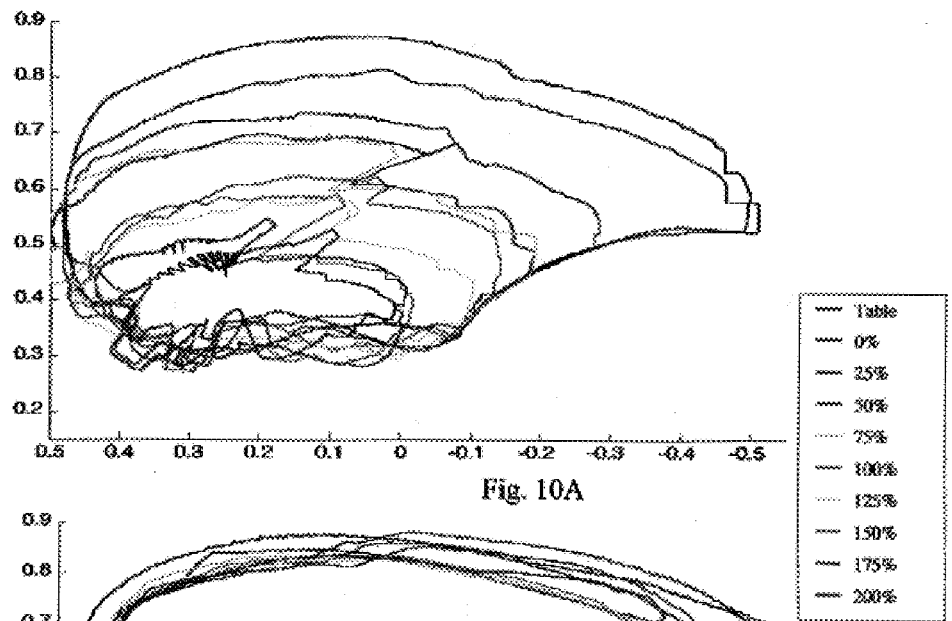
FIG. 10 illustrates exemplary results from an experiment that tested the work area of a left hemiparetic subject.
Figure 10B:
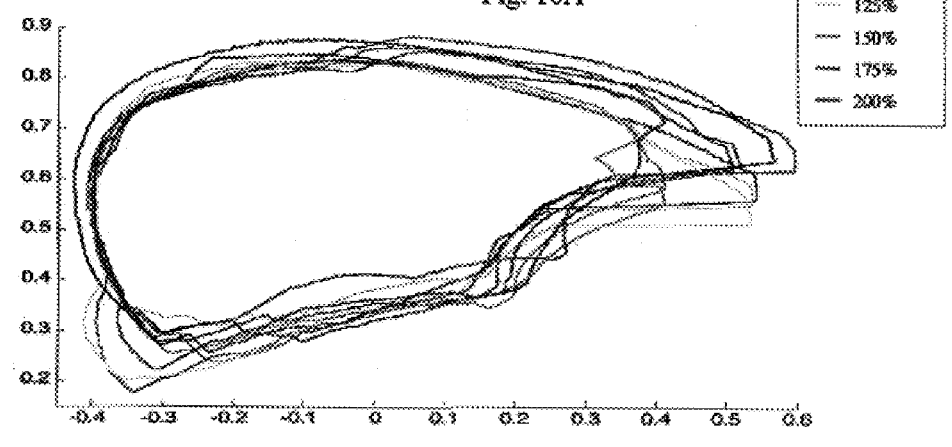
Figure 11:
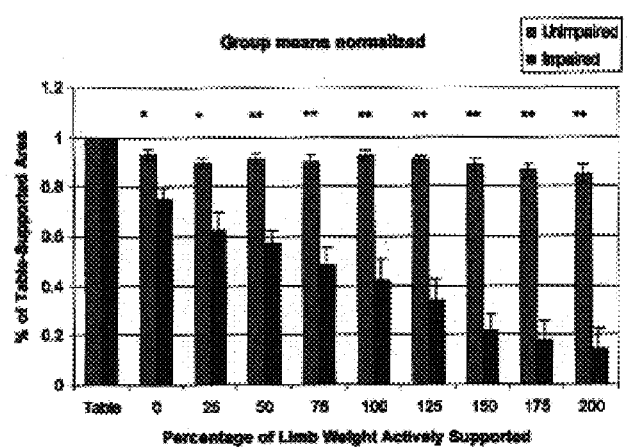
FIG. 11 shows the cumulative data for experiments that tested the work area of hemiparetic subjects. (*$p<0.05$; **$p<0.001$).

To reduce the impact that hyperexcitable stretch reflexes (or spasticity) may also have on the compromised arm, another protocol emphasizes slow movements. Subjects were asked to slowly make the largest circle they could with their arm. Like the ballistic reaching protocol, this was done under rigid support from a haptic table, or while the subject was concurrently producing particular levels of active limb support. By reducing the impact of spacticity, the best picture of available work area was constructed. We conducted some experiments using the above protocol with adult hemiparetic stroke subjects; FIG. 10 shows an example of the results obtained. FIG. 10A shows work areas a left hemiparetic subject was able to achieve with their impaired limb (the x-axis has been inverted for comparison with the right side). As active limb support increases, there is a marked decrease in available work area. FIG. 10B shows the results from their unimpaired side. In the unimpaired side, there was no effect of limb support (FIG. 10B). However, in the impaired side there was a clear cost for increased levels of active limb support, and therefore shoulder abduction torques (FIG. 10A). Work area decreased significantly as subjects were required to lift more of their limb weight; this was a direct effect of decreases in elbow extension range as illustrated on FIG. 11 for twelve moderate-to-severely impaired stroke subjects, with elbow flexion capabilities preserved across support levels. FIG. 11 compares the unimpaired (left bar, blue) and impaired (right bar, red) limb work areas, normalized to the table supported condition revealed a significant difference between limbs in all levels of support (*p<0.05; ** p<0.001).

The results were obtained at the horizontal plane at 90 degrees of shoulder abduction. This protocol-can be extended into inclined and declined planes in the same way as the ballistic reaching protocol. Using the information collected by the $ACT^{3D}$, a complete characterization of available shoulder and elbow angle and torque combinations and resulting 3-D workspace during different levels of support and at different plane inclination angles were constructed for each subject.

Example III

Therapeutic Intervention

Figures 12A, 12B:
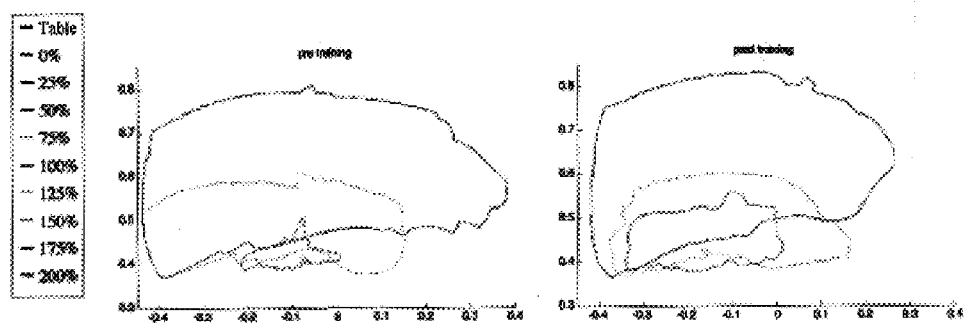
FIG. 12 shows the results for experiments that tested the work area before (12A) and after (12B) training.

Under the guidance of our gravity-induced discoordination concept, several therapeutic intervention protocols can be realized. A protocol in which gravity was progressively re-introduced during outward reaching over a period of eight weeks was used. More specifically, subjects were trained to reach outward towards virtually displayed targets that were situated on a horizontal plane associated with the height of the shoulder. The targets required near full active range of motion to acquire. The key component of the training was the progressive re-introduction of gravity as the subject improved in their capacity to acquire each target. Furthermore, gravity was re-introduced in an aggressive fashion. Subjects performed three sets of ten repetitions to each of five targets under the amount of gravity or limb support that maximally challenged them to reach at least 50% of the distance toward the target. Each target ultimately had its own gravity setting and appeared to progress at its own rate in terms of increasing the gravity setting on the following session as the subject was able to reach farther toward the target. The effect of gravity re-introduction training on motor performance is studied by comparing this protocol with a similar protocol where active support of the limb against gravity is not required. In this comparison group, subjects reach toward the same targets but are supported by a haptically rendered horizontal surface associated with the height of the shoulder. Each group participates in eight weeks of training at a frequency of three sessions per week. By comparing group performance on the metrics mentioned in the previous section, the effect of re-introducing gravity is elucidated. An example of a positive effect of the gravity reintroduction protocol is shown for a single subject in FIG. 12. FIG. 12 shows hand path traces pre (FIG. 12A) and post (FIG. 12B) training, with three support levels shown. Note the increase in work area at 175% of limb weight using the work area measurement discussed earlier.

Example IV

Interface Between the Paretic Limb and the HAPTICMASTER

The forearm of the stroke survivor was placed on a support splint that was attached via a three degree-of-freedom (3-DOF) gimbal axis system to the end of the robot. The elbow was lined up with the vertical axis of the gimbal (see FIG. 6). A 6-DOF load cell was placed between the support splint and the gimbal to measure the shoulder abduction/adduction and internal/external rotation torques. Furthermore, the gimbal was instrumented with position sensors used to measure the elbow and shoulder rotation angles. The mechanical interface was designed to constrain movements to a plane such that the individual moves (reaching or retrieving) his/her arm and hand in line with the shoulder. The inclination of the plane was adjustable from the user interface to different angles, resulting in upward or downward arm movements with respect to the shoulder. This accommodated individuals with limited shoulder abduction angles and allowed for a progression to greater shoulder abduction angles over various training sessions. Support splints were designed for the left and the right arm and were made in a small and large size to accommodate individuals of different sizes (see FIG. 6). The support splint can be attached and detached from the robot using a quick release type system. The position of the hand and wrist in the splint was such that it reduces spastic activity in hand and wrist flexors. Finally, the hand and forearm were secured to the splint using broad, stiff VELCRO straps.

Example V

Interface Between HAPTICMASTER, Biodex Experimental Chair, and Visual 3-D Display In this Example, the robotic device was designed into a single unit integrating three separate systems: a Biodex chair, a HAPTICMASTER device and a standard 19" LCD screen (Dell, Round Rock Tex.) controlled via a computer interface. The system was a self-contained unit that could be easily operated by therapists and physicians both for patient testing setup and for designing and running therapeutic sessions.

The HAPTICMASTER device was placed on a T support track that allows a Biodex chair and 3-D robot to move relative to each other and to rotate (FIG. 5 and FIG. 15). This enabled proper alignment between the robot and the arm of the individual. The HAPTICMASTER device and its controller box were consolidated into one unit to reduce the overall size of the setup. Finally, a standard 19" screen (Dell) was attached on a mobile multi-jointed arm that was connected to the back of the Biodex chair. This allowed flexibility in the positioning of the 3-D screen in the visual field of test participants.

Example VI

User Interface and Visual Virtual Reality Software

The robotic device was controlled via a custom user interface developed to allow simple operation of the device. The user interface software allowed control of the robotic device during reaching movements and specification of the training and evaluation protocols.

In order to create a realistic environment for individuals with stroke, 3-D visual feedback was incorporated into the system. In this example, a standard 19" LCD screen that provided a 3-D image based on the principle of autostereoscopic 3D imaging is used. The position signals of the robotic device combined with the segment lengths of the arm were used to estimate the paretic arm configuration. These configuration coordinates drive the position of a virtual arm/hand on the 3D screen in real-time. When designing a 3D model of the arm, a standard modeling package like Kinetix's 3D STUDIO MAX may be used. In this example, the model was driven in Windows XP environment using the Win3D Library, compatible with the DTI technology. The virtual visual environment also included the plane of the virtual table, movement targets and realistic objects that can be lifted and moved to targets like a video game. The intent was to create a stimulating and realistic environment that would motivate our stroke consumers to use their paretic arm and to teach them how to progressively overcome the negative effect of gravity in a functionally meaningful way.

Example VII

Additional Exemplary Embodiments

As noted above, other configurations of the haptics device are possible. FIG. 15 shows one such example of a 3-D haptic device concept where the axes are fully independent.

Figure 8:
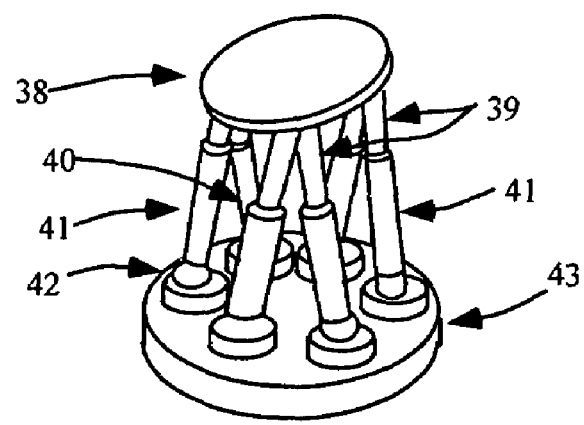
FIG. 8 illustrates an alternative embodient of the gravity negating means, a Stewart platform.

Another example that is far more complex is a Stewart platform shown in FIG. 8. This is used extensively in Flight Simulators to provide motion sensation to the pilots. The hexapod structure uses six actuators, and is thus capable of providing 6-DOF motion. In our situation the end effector and associated additional hardware could be mounted on the top platform.

FIG. 9 shows a prototype of 3-D visual feedback displaying an avatar of the subject's arm. The tip of the virtual hand is placed in a starting position (gray hemisphere) and the subject is asked to move the hand to one of the targets (blue hemispheres). The red boundary is the maximum reaching distance of the subject's hand based on measured forearm/ upper arm segment lengths. This boundary is use as visual feedback to encourage subjects to reach as far as they can to determine the arm active work area. This can be repeated for different planes to determine the paretic arm's workspace.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A method for measuring, treating, and self-rehabilitating an individual having a neurological condition, the method comprising:
   i) providing a system comprising mechanical means, at least one computer, display means, and interconnecting means, the mechanical means further comprising an interacting instrumented member that interacts with the body or a part thereof of the individual, a force sensor, a force generator, at least one moveable non-compliant linkage, and a base, the force sensor further being attachedly connected by the linkage to the force generator, the linkage having at least three degrees of freedom, the computer further comprising an interactive software program, and the base supporting at least one of the above;
   ii) securing a body or part thereof of the individual to the interacting instrumented member;
   iii) permitting the individual to move the body or part thereof to a desired position;
   iv) sensing the force required to move the body or part thereof using the force sensor;
   v) producing force input data using the sensed force;
   vi) transmitting the force input data from the force sensor to the computer;
   vii) processing the force input data using the interactive software program;
   viii) transmitting the processed data to the display means whereby the display shows a virtual environment;
   ix) processing the data to produce force output data;
   x) transmitting the force output data to the force generator and the linkage thereby generating a force upon the interacting instrumented member and the body or part thereof, the resulting generated force upon the body or part thereof causing the muscles and nerves in the body or part thereof to be stimulated, the stimulation resulting in regaining muscle coactivation patterns and associated joint torques patterns for the individual; thereby measuring, treating, and self-rehabilitating the individual.

2. The method of claim 1 wherein the body or part thereof is selected from the group consisting of a whole body, a trunk, a shoulder, a neck, a head, an arm, an elbow, a wrist, a hand, a hip, a leg, a knee, an ankle, and a foot.

3. The method of claim 1 wherein the interconnecting means provide radio communicating signals, electrical communicating signals, photonic communicating signals, or a combination thereof, between the mechanical means, the computer, and the display means.

4. The method of claim 1 wherein the force generator is an actuator selected from the group consisting of a rotary hydraulic motor, a linear hydraulic motor, a pneumatic motor, and an electric motor.

5. The method of claim 1 wherein the method further comprises the step of attaching at least one position measurement device, the position measurement device being placed on a predetermined position selected from the group consisting of an end effector, a linkage, a force sensor, a force generator, a shoulder, a hip, a neck, and a head.

6. The method of claim 1 wherein the generated force compensates for the force due to gravity on the body or part thereof and wherein the generated force is equivalent in magnitude to between about −1 times and about +4 times the force of gravity upon the body or part thereof.

7. The method of claim 1 wherein the generated force is essentially equivalent to a force required for manipulating joint abduction torques of the individual, the joint selected from the group consisting of the shoulder and the hip.

8. The method of claim 1 wherein the interacting instrumented member further comprises a sensor selected from the group consisting of a force sensor, a position sensor, and a motion sensor.

9. The method of claim 1 wherein the interacting instrumented member further comprises an electrical stimulator, the electrical stimulator being further releasably connected to an extremity of the body or part thereof.

10. The method of claim 9 wherein the electrical stimulator stimulates movement in the extremity of the body, the extremity being selected from the group consisting of a finger, a thumb, a hand, an elbow, a shoulder, a wrist, a toe, a foot, an ankle, a knee, and a hip.

11. The method of claim 9 wherein the interacting instrumented member comprises a member selected from the group consisting of a splint, a limb support, a hand support, a foot support, and a force-sensing treadmill.

12. The method of claim 10 wherein the stimulated movement results in a propriosensory effect in the individual.

13. The method of claim 10 wherein the stimulated movement results in a dermal tactile sensory effect in the individual.

14. The method of claim 10 wherein the stimulated movement results in a muscle sensory effect in the individual.

15. The method of claim 1 wherein the neurological condition is selected from the group consisting of hemiparetic stroke, cerebral palsy, head trauma, and multiple sclerosis.

16. The method of claim 1 wherein the neurological condition results in a loss of independent joint control in the body or part thereof.

17. The method of claim 1 wherein the system further comprises an end effector articulatedly attached between an appendage attaching member and the force generator.

18. The method of claim 1 further comprising a step of determining a position of an appendage attaching member to generate a position data and providing the position data to the computer and the display means.

19. The method of claim 1 wherein the computer further comprises memory means for storing the force input data, the virtual environment, a position data, and the force output data.

* * * * *